United States Patent
Webb et al.

(10) Patent No.: US 11,807,675 B2
(45) Date of Patent: Nov. 7, 2023

(54) NANOPARTICLE BASED ARTIFICIAL ANTIGEN PRESENTING CELL MEDIATED ACTIVATION OF NKT CELLS

(71) Applicant: University of Maryland, Baltimore, Baltimore, MD (US)

(72) Inventors: Tonya Webb, Glen Burnie, MD (US); Carolyn Morris, Evergreen, CO (US); James East, Carrboro, NC (US)

(73) Assignee: The University of Maryland, Baltimore, Baltimore, MD (US)

( * ) Notice: Subject to any disclaimer, the term of this patent is extended or adjusted under 35 U.S.C. 154(b) by 680 days.

(21) Appl. No.: 15/027,148

(22) PCT Filed: Oct. 3, 2014

(86) PCT No.: PCT/US2014/059038
§ 371 (c)(1),
(2) Date: Apr. 4, 2016

(87) PCT Pub. No.: WO2015/051247
PCT Pub. Date: Apr. 9, 2015

(65) Prior Publication Data
US 2016/0237137 A1    Aug. 18, 2016

Related U.S. Application Data

(60) Provisional application No. 61/886,187, filed on Oct. 3, 2013.

(51) Int. Cl.
| | |
|---|---|
| *A61K 9/14* | (2006.01) |
| *A61K 9/16* | (2006.01) |
| *A61K 47/69* | (2017.01) |
| *A61K 49/18* | (2006.01) |
| *C07K 17/14* | (2006.01) |
| *C07K 14/74* | (2006.01) |
| *C12N 5/0783* | (2010.01) |
| *C07K 16/00* | (2006.01) |

(52) U.S. Cl.
CPC .... *C07K 14/70539* (2013.01); *A61K 49/1866* (2013.01); *A61K 49/1875* (2013.01); *C07K 16/00* (2013.01); *C12N 5/0646* (2013.01); *C07K 2317/51* (2013.01); *C07K 2319/00* (2013.01)

(58) Field of Classification Search
None
See application file for complete search history.

(56) References Cited

U.S. PATENT DOCUMENTS

2011/0256147 A1    10/2011 Delke et al.

FOREIGN PATENT DOCUMENTS

WO    2013086500 A1    6/2013

OTHER PUBLICATIONS

Oelke et al (Nat. Med. 2003, 9(5): 619-624) (Year: 2003).*
DynabeadsTM Products & Technology (ThermoFisher Scientific, 2019, 5 pages) (Year: 2019).*
DynabeadsTM M-450 Epoxy (ThermoFisher Scientific, 2019, 5 pages) (Year: 2019).*
Uldrich et al (J. Immunol. 2005, 175: 3092-3101) (Year: 2005).*
Sun et al (J. Interfer. Cyto. Res., 2012 32(11): 505-516) (Year: 2012).*
Parekh et al (Int. Rev. Immunol., 2007, 26: 31-48) (Year: 2007).*
Hwang and Foote (Methods, 2005, 36: 3-10) (Year: 2005).*
Extended European Search Report for correspondence EP Application 14850522.5 dated Jun. 6, 2017, pp. 1-7.
Sun, et al., Connecting the Dots: Artificial antigen presenting cell-mediated modulation of natural killer T cells, "J. interferon & cytokine res.", vol. 32, Issue 11, pp. 505-516 (2012).
Karlo, et al., Abstract 4531: Nanoscale artificial antigen presenting cells for t cell immunotherapy, "Cancer res.", vol. 73, Issue 8 (2013).
Berzins, S.P., et al. "Presumed guilty: natural killer T cell defects and human disease," Nat Rev Immunol, 2011, pp. 131-142, vol. 11.
Bessoles, S., et al. "IL-2 triggers specific signaling pathways in human NKT cells leading to the production of pro- and anti-inflammatory cytokines," J Leukoc Biol, 2008, pp. 224-233, vol. 84.
Carnaud, C., et al. "Cutting edge: Cross-talk between cells of the Innate Immune System: NKT Cells Rapidly Activate NK Cells," J Immunol, 1999, pp. 4647-4650, vol. 163.
East, E.E., et al. "Artificial Antigen Presenting Cell (aAPC) Mediated Activation and Expansion of Natural Killer T Cells," J of Vis. Exp., 2012, pp. 1-6 , vol. 70.
Exley, M., et al. "CD161 (NKR-PIA) Costimulation of CD1d-dependent Activation of Human T Cells Expressing Invariant Va24JaQ T Cell Receptor a Chains," J. Exp. Med., 1998, pp. 867-876, vol. 188.
Fujii, S., et al. "Activation of Natural Killer T Cells by a-Galactosylceramide Rapidly Induces the Full Maturation of Dendritic Cells in Vivo and Thereby Acts as an Adjuvant for Combined CD4 and CD8 T Cell Immunity to a Coadministered Protein," J. Exp. Med., 2003, pp. 267-279, vol. 198.
Goff, R.D., et al. "Effects of Lipid Chain Lengths in a-Galactosylceramides on Cytokine Release by Natural Killer T Cells," J. Am. Chem. Soc., 2004, pp. 13602-13603, vol. 126.
Goldberg, B., et al. "Dimeric MHC-peptides inserted into an immunoglobulin scaffold as new immunotherapeutic agents," J. Cell. Mol. Med., 2011, pp. 1822-1832, vol. 15.
Goldberg, J., et al. "In Vivo Augmentation of Tumor-Specific CTL Responses by Class I/Peptide Antigen Complexes on Microspheres (Large Multivalent Immunogen)," J. Immunol., 2003, pp. 228-235, vol. 170.

(Continued)

*Primary Examiner* — G. R. Ewoldt
*Assistant Examiner* — Marianne DiBrino
(74) *Attorney, Agent, or Firm* — Wolter Van Dyke Davis, PLLC; Eugene J. Molinelli; Martha Cassidy

(57) ABSTRACT

The present invention relates to, in part, artificial antigen presenting cells that are useful in treating disease (including cancers) and have uses, for example, directly in vivo and/or in the expansion of a patients cells for re-introduction ex vivo.

10 Claims, 27 Drawing Sheets
Specification includes a Sequence Listing.

(56) References Cited

OTHER PUBLICATIONS

Kim, C.H., et al. "Trafficking machinery of NKT cells: shared and differential chemokine receptor expression among Va24+VB11+ NKT cell subsets with distinct cytokine-producing capacity," Blood J., 2002, pp. 11-16 Volume 100.

Kinjo, Y., et al., "Recognition of bacterial glycosphingolipids by natural killer T cells," Nature, 2005, pp. 520-525, vol. 434.

Koch, M., et al., "The crystal structure of human CD1d with and without a-galactosylceramide," Nat. Immunol., 2005, pp. 819-826, vol. 6.

Fernandez E. M., et al. "Activation of invariant Natural Killer T lymphocytes in response to the a-galactosylceramide analogue KRN7000 encapsulated in PLGA-based nanoparticles and microparticles," Int. J. Pharm., 2012, pp. 45-54, vol. 423.

Maus, M.V., et al., "Ex vivo expansion of polyclonal and antigen-specific cytotoxic T lymphocytes by artificial APCs expressing ligands for the T-cell receptor, CD28 and 4-1BB," Nat. Biotechnol., 2002, pp. 143-148, vol. 20.

Oelke, M., et al., "Ex vivo induction and expansion of antigen-specific cytotoxic T cells by HLA-Ig-coated artificial antigen-presenting cells," Nat. Med., 2003, pp. 619-625, vol. 9.

Salvador, A., et al., "Combination of immune stimulating adjuvants with poly(lactide-co-glycolide) microspheres enhances the immune response of vaccines," Vaccine, 2012, pp. 589-596, vol. 30.

Schutz, C., et al., "Killer artificial antigen-presenting cells: a novel strategy to delete specific T cells," Blood J., 2008, pp. 3546-3552, vol. 111.

Shiratsuchi, T., et al., "Human CD1 dimeric proteins as indispensable tools for research on CD1-binding lipids and CDI-restricted T cells," J. Immunol. Methods, 2009, pp. 49-59, vol. 345.

Subrahmanyam, P. B., et al., "Boosting the immune response: the use of iNKT cell ligands as vaccine adjuvants," Frontiers in Biology, 2012, pp. 436-444, vol. 7.

Tham, E.L., et al., "Activation of antigen-specific T cells by artificial cell constructs having immobilized multimeric peptide-class I complexes and recombinant B7-Fc proteins," J. Immunol. Methods, 2001, pp. 111-119, vol. 249.

Turtle, C.J., et al., "Artificial antigen-presenting cells for use in adoptive immunotherapy," Cancer J. 2010, pp. 374-381, vol. 16.

Webb, T.J., et al., "Ex vivo induction and expansion of natural killer T cells by CD1d1-Ig coated artificial antigen presenting cells," J. Immunol. Methods, 2009, pp. 38-44, vol. 346.

Yu, K.O.A., et al., "Modulation of CD1d-restricted NKT cell responses by using N-acyl variants of a-galactosylceramides," Proc. Natl. Acad. Sci. USA, 2005, pp. 3383-3388, vol. 102.

International Search Report and Written Opinion, International Patent Application No. PCT/US2014/059038, dated Jan. 14, 2015, pp. 1-13.

East, J.E., et al., "Raising the Roof: The Preferential Pharmacological Stimulation of Th1 and Th2 Responses Medicated by NKT Cells," Med. Res. Reviews, 34, No. 1, 45-76, 2014.

* cited by examiner

NANOPARTICLE BASED ARTIFICIAL ANTIGEN PRESENTING CELL MEDIATED ACTIVATION OF NKT CELLS

CROSS-REFERENCE TO RELATED APPLICATION

This application is a 371 national stage application of PCT Application No. PCT/US14/59038, filed Oct. 3, 2014, and claims the benefit of Provisional Application No. 61/886,187, filed Oct. 3, 2013, under 35 U.S.C. § 119(e), the entire contents of each application are hereby incorporated by reference as if fully set forth herein.

STATEMENT OF GOVERNMENT INTEREST

This invention was made with government support under Grant Numbers CA131487, CA162273, CA162277, and CA134274 awarded by the National Institutes of Health. The government has certain rights in the invention.

REFERENCE TO SEQUENCE LISTING

This application is includes an electronically submitted sequence listing in .txt format. The .txt file contains a sequence listing entitled "15024-304U51_ST25.txt" created on Jun. 22, 2022 and is 553 bytes in size. The sequence listing contained in this .txt file is part of the specification and is hereby incorporated by reference herein in its entirety.

FIELD OF THE INVENTION

The present invention provides, among other things, compositions and methods that are useful in, for example, immunotherapies.

BACKGROUND

The interaction between various diseases, including cancer, and the immune system is complex and multifaceted. For example, while many cancer patients appear to develop an anti-tumor immune response, cancers also develop strategies to evade immune detection and destruction. Immunotherapies have been pursued for the treatment and prevention of cancer and other disorders.

Natural killer T (NKT) cells are a heterogeneous group of immune cells that share properties of both T cells and natural killer (NK) cells and recognize the non-polymorphic CD1d molecule, an antigen-presenting molecule that binds self and foreign lipids and glycolipids. Immunotherapy approaches with these cells or their cognate antigens have been limited. There is a need in the art for an effective means of generating therapeutically useful populations of NKT cells, either in vivo or ex vivo.

SUMMARY OF THE INVENTION

In some aspects, the invention provides artificial antigen presenting cells (aAPCs) that activate and/or generate NKT cells from samples comprising NKT cells or precursor cells. The aAPCs may be microparticles or nanoparticles, and comprise a population of NKT cell activating ligands on their surface. For example, such ligands may be based on the CD1d antigen presenting complex. The CD1d presents NKT cell antigens, such as α-GalCer, α-C-GalCer, —OCH, GSL-1, and iGB3, among others. In some embodiments the CD1d is a fusion protein with immunoglobulin heavy chain sequences (e.g., IgG), providing for dimeric CD1d complexes. The aAPCs further comprise a population of at least one NKT cell co-stimulatory ligand, such as an antibody against CD28, CD44, CD40, or CD161. In some embodiments, the antibody is an antibody fragment or antigen-binding derivative, such as, a F(ab')2, a Fab, scFv, or a single chain antibody.

In various embodiments, particle substrates include Quantum dots, paramagnetic beads, and polymeric particles. In various embodiments, the particle has a size of within about 10 to about 500 nm.

The invention further provides pharmaceutical compositions comprising the aAPCs, including for various routes of administration, including parenteral administration, enteral administration, or administration to a mucous membrane, such as intranasal administration.

In some aspects, the invention provides methods for treatment of disease in which production of NKT cells would be beneficial, such as cancer, autoimmune disease, or infectious disease. In these aspects, the aAPCs may be administered to patients to stimulate production and/or activate NKT cells in vivo.

In still other aspects, the invention provides methods for generating NKT cells from patient samples ex vivo, which may be used for adoptive immunotherapy in some embodiments. For example, NKT cells may be generated from peripheral blood mononuclear cell (PBMC), bone marrow, lymph node tissue, spleen tissue, or a tumor sample, and administered back to the patient in some embodiments.

In some embodiments, the invention involves quantum dot based-artificial antigen presenting complexes (Qdot-aAPC) that can be used to specifically expand NKT cells, including in vivo or ex vivo from adult bone marrow derived progenitors. Qdot-aAPCs may be administered to patients in some embodiments, including through the intranasal route, for in vivo generation and/or activation of NKT cells. The Qdot-aAPCs are loaded with antibodies against NKT cell targets that result in activation (such as anti-CD28 or anti-CD44), as well as dimeric CD1d-Ig fusion proteins that present NKT cell target antigens. In some embodiments, NKT cells are generated ex vivo in the presence of OP9-DL1 feeder cells, and the cells or a population of the cells administered to the patient for adoptive immunotherapy. In some embodiments, the NKT cells generated work synergistically with antigen-specific CD8+ cells, which can be expanded for adoptive transfer in parallel or simultaneously.

DETAILED DESCRIPTION

Figure 1:
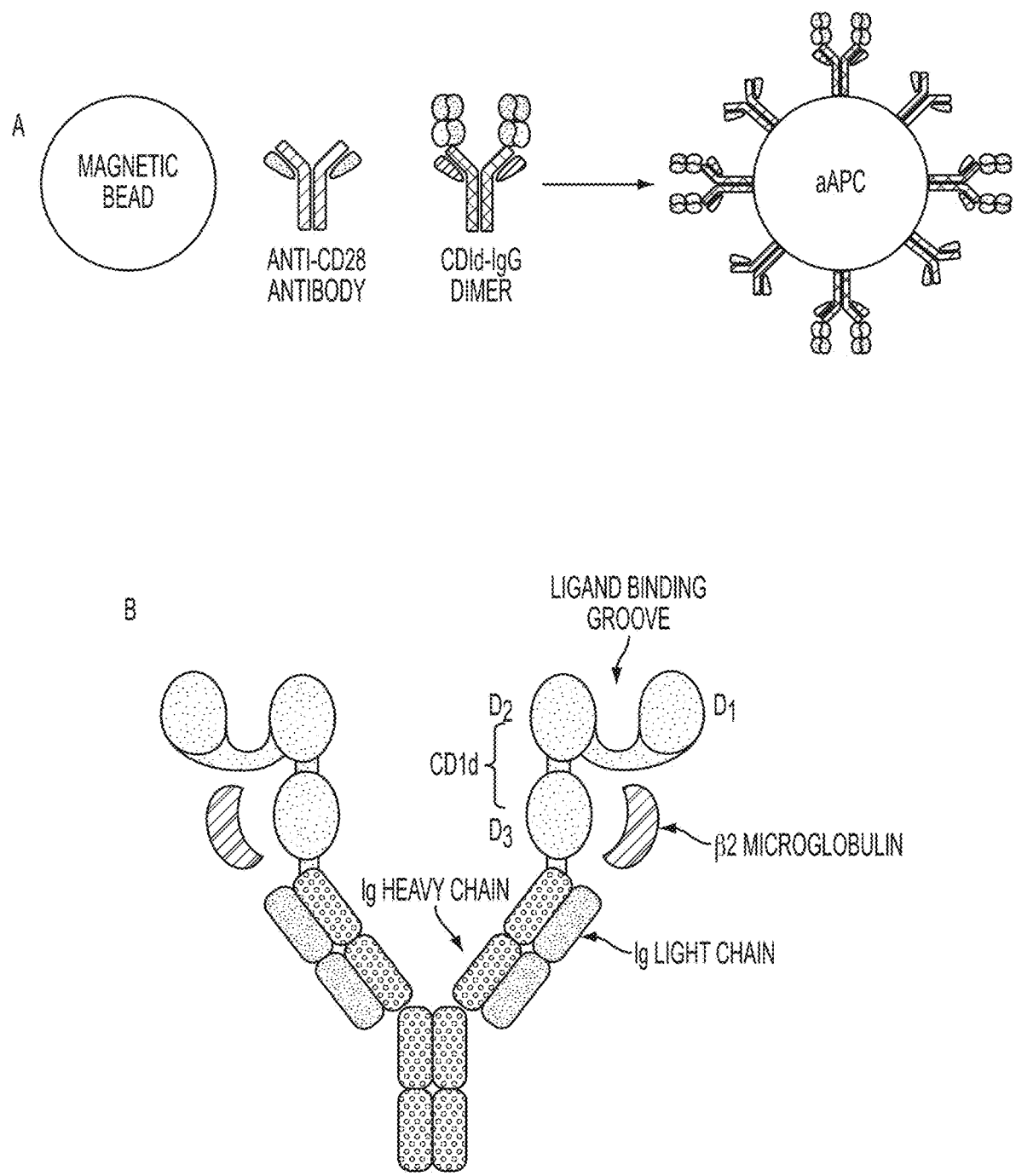
FIG. 1, Panel A shows a schematic diagram of CD1d:Ig-based aAPBC. Panel B shows a schematic diagram of CD1d-Ig. Extracellular portions of the CD1d molecule are fused to the constant region of an immunoglobulin heavy chain protein separated by a short amino acid linker. These fusion proteins are expressed in eukaryotic cells, so that denaturing and refolding is not necessary. Also, these molecules can be easily loaded with lipid antigens, such as α-GalCer, simply by incubating them with an excess of the lipid of interest.

In various aspects, the invention provides artificial antigen presenting cells (aAPCs) that activate and/or generate NKT cells from samples comprising NKT cells or precursor cells, and pharmaceutical compositions comprising the same. The aAPCs may be microparticles or nanoparticles, and comprise a population of NKT cell activating ligands on their surface. In still other aspects, the invention provides methods for generating NKT cells from patient samples ex vivo, which may be used for adoptive immunotherapy in some embodiments. For example, NKT cells may be generated from peripheral blood mononuclear cell (PBMC), bone marrow, lymph node tissue, spleen tissue, or a tumor sample, and administered back to the patient in some embodiments.

aAPCs have potential clinical value for in vivo or ex vivo expansion of antigen specific T cells as part of an adoptive immunotherapy regimen, as well as their ability to delineate basic requirements for T cell activation. In various embodiments, the aAPC is bead-based (e.g. quantum dots, magnetic beads, polymeric or latex microspheres, etc.). In various embodiments, the non-cellular bead based aAPC of the present invention is made by coupling CD1d, signal 1, and anti-CD28 or other co-stimulatory signal, signal 2, onto the microparticle or nano-particle surface. The CD1d may be conjugated as an Ig fusion, which provides a unique multimeric form having the immunoglobulin molecular scaffold, which takes advantage of the intrinsic flexibility associated with Ig proteins for expression of a dimeric complex. Based on their valence, these molecules can be used to stimulate antigen-specific T cells and can be derivatized to solid supports such as beads based on the Ig domains.

In some embodiments, the present invention provides a CD1d-Ig based aAPC, which can optionally be used to replace autologous α-GalCer pulsed DC to generate effector NKT cells for adoptive immunotherapy. Since the engagement of the T cell receptor (TCR) by the CD1d-antigen complexes is a fundamental requirement of NKT cell activation, antigen:CD1d-Ig complexes, along with appropriate costimulatory molecules, offer a reliable method to isolate, activate, and expand effector NKT cell populations. In some embodiments, the present invention provides methods for enhancing immunotherapy and/or stimulating NKT cells by contacting a cell with a CD1d-Ig based aAPC, which in some embodiments comprises a covalent coupling of CD1d-Ig and anti-CD28 mAb to a quantum dot, magnetic bead, or polymeric particle. In various embodiments, the CD1d-Ig based aAPC can be used in the treatment of cancers as described herein, including but not limited to inhibition of tumor metastasis. Such methods can comprise administering a therapeutically effective amount of the CD1d-Ig based aAPC to the patient and/or a population of a patient's cells (e.g. T cells) expanded with the CD1d-Ig based aAPC.

In some embodiments, the ratio of CD1d-Ig to anti-CD28 is: about 30:1, about 10:1, about 3:1, about 1:1, about 0.3:1, about 0.1:1, or about 0.03:1.

Accordingly, in some embodiments, there are provided therapeutic methods that comprise adoptive immunotherapy with the aAPC described herein, which generate NKT cells, as well as with tumor specific T cells (e.g., CTLs). Adoptive immunotherapy involves stimulation of the NKT cells and tumor-specific T cells, ex vivo, followed by transfer of expanded numbers of activated cells back into patients. In some embodiments, stimulation is via the present aAPCs. In some embodiments, without wishing to be bound by theory, the ex vivo expanded autologous cells traffic to tumor sites and directly induce tumor shrinkage. In some embodiments, without wishing to be bound by theory, the ex vivo expanded cells cause a regression of metastatic tumors.

In various embodiments, the present aAPCs comprise a bead, which may be a microscale or nanoscale bead. In various embodiments, the bead has a size (e.g., average diameter) within about 10 to about 500 nm, or within about 20 to about 300 nm, such as about 20 nm, about 50 nm, about 100 nm, about 150 nm, or about 200 nm.

In some embodiments, the bead that serves as a synthetic core includes, but is not limited to Quantum Dots (Q-dots). A quantum dot is a nanocrystal made of semiconductor materials that is small enough to exhibit quantum mechanical properties. Specifically, its excitons are confined in all three spatial dimensions. The electronic properties of these materials are intermediate between those of bulk semiconductors and of discrete molecules.

In various embodiments, the bead has magnetic properties. Paramagnetic materials have a small, positive susceptibility to magnetic fields. These materials are attracted by a magnetic field and the material does not retain the magnetic properties when the external field is removed. Illustrative paramagnetic materials include, without limitation, magnesium, molybdenum, lithium, tantalum, and iron oxide. Paramagnetic beads suitable for magnetic enrichment are commercially available (DYNABEADS™, MACS MICROBEADS™, Miltenyi Biotec). In some embodiments, the aAPC bead is an iron dextran bead (e.g., dextran-coated iron-oxide bead). In certain aspects of the invention, for example, where magnetic properties are not required, beads can be made of nonmetal or organic (e.g., polymeric) materials such as cellulose, ceramics, glass, nylon, polystyrene, rubber, plastic, or latex. In various embodiments, the beads are polymeric, and comprise PLGA polymers or copolymers thereof.

Molecules can be directly attached to beads by adsorption or by direct chemical bonding, including covalent bonding. See, Hermanson, BIOCONJUGATE TECHNIQUES, Academic Press, New York, 1996, which is hereby incorporated by reference in its entirety. A molecule itself can be directly activated with a variety of chemical functionalities, including nucleophilic groups, leaving groups, or electrophilic groups. Activating functional groups include alkyl and acyl halides, amines, sulfhydryls, aldehydes, unsaturated bonds, hydrazides, isocyanates, isothiocyanates, ketones, and other groups known to activate for chemical bonding. Alternatively, a molecule can be bound to a bead through the use of a small molecule-coupling reagent. Non-limiting examples of coupling reagents include carbodiimides, maleimides, n-hydroxysuccinimide esters, bischloroethylamines, bifunctional aldehydes such as glutaraldehyde, anyhydrides and the like. In other embodiments, a molecule can be coupled to a bead through affinity binding such as a biotin-streptavidin linkage or coupling, as is well known in the art. For example, streptavidin can be bound to a bead by covalent or non-covalent attachment, and a biotinylated molecule can be synthesized using methods that are well known in the art.

If covalent binding to a bead is contemplated, the support can be coated with a polymer that contains one or more chemical moieties or functional groups that are available for covalent attachment to a suitable reactant, typically through a linker. For example, amino acid polymers can have groups, such as the ε-amino group of lysine, available to couple a molecule covalently via appropriate linkers. This disclosure also contemplates placing a second coating on a bead to provide for these functional groups.

Activation chemistries can be used to allow the specific, stable attachment of molecules to the surface of bead. There are numerous methods that can be used to attach proteins to functional groups. For example, the common cross-linker glutaraldehyde can be used to attach protein amine groups to an aminated bead surface in a two-step process. The resultant linkage is hydrolytically stable. Other methods include use of cross-linkers containing n-hydrosuccinimido (NHS) esters which react with amines on proteins, cross-linkers containing active halogens that react with amine-, sulfhydryl-, or histidine-containing proteins, cross-linkers containing epoxides that react with amines or sulfhydryl groups, conjugation between maleimide groups and sulfhydryl groups, and the formation of protein aldehyde groups by periodate oxidation of pendant sugar moieties followed by reductive amination.

As described herein, CD1 antigen presenting complexes, including CD1d (e.g., CD1d-Ig fusions) can be conjugated to beads to generation and/or activation of NKT cells.

In humans, five genes (CD1A-E) located within 200-kb on chromosome 1q22-q23 encodes CD1a, CD1b, CD1c, CD1d and CD1e lipid antigen-presenting molecules. The CD1 proteins that are classified into two groups based on amino acid sequence homology: group 1 is composed of CD1a, b, c, and e; and group 2 contains CD1d. Like MHC Class I molecules, CD1 isoforms (CD1a, b, c and d) are assembled in the ER and transported to the cell surface. However, in contrast to MHC molecules, CD1 complexes are then re-internalized into specific endocytic compartments where they can bind lipid antigens. These include a broad scope of both self and foreign molecules that range from simple fatty acids or phospholipids, to more complex glycolipids, isoprenoids, mycolates and gangliosides. Lipid-loaded CD1 molecules are then delivered to the cell surface and can be surveyed by CD1-restricted T cells expressing αβ or γδ T cell receptors (TCR). CD1a, b and c-restricted T cells have been found to recognize a number of lipid antigens from *M. tuberculosis*. Mice only express group 2 CD1d molecules-CD1d1 and CD1d2. iNKT cells are CD1d1-restricted and the focus of this review. Notably, the crystal structures of both mouse and human CD1d have been described. These studies have shown that the antigen binding groove is deeper, narrower, and much more hydrophobic compared to MHC class I and class II molecules. The hydrophobic nature of the antigen binding groove is ideal for binding lipid antigens. In vitro binding studies have determined the molecular mechanism for lipid antigen presentation by CD1 molecules: the alkyl chains of a lipid-ligand bind within a highly hydrophobic groove inside the CD1 protein while the polar head group remains exposed on top of the extracellular domain, thereby allowing direct contact with the TCR, leading to NKT cell activation.

In some embodiments, the "costimulatory molecule" or a "costimulatory polypeptide" is a polypeptide that, upon interaction with a cell-surface molecule on T cells, enhances T cell responses, enhances proliferation of T cells, enhances production and/or secretion of cytokines by T cells, stimulates differentiation and effector functions of T cells or promotes survival of T cells relative to T cells not contacted with a costimulatory molecule.

In some embodiments, the costimulatory molecule(s) includes, but is not limited to an antibody or antigen-binding fragment or derivative of the following target ligands: CD28, CD44, CD161, CD69, 41 BB, CD161, or OX40L.

In some embodiments, an NKT cell agonist can be loaded onto the aAPC. The agonist can include, but is not limited to a lipid or glycolipid antigen. In some embodiments the agonist is selected from the soluble lipid antigen α-GalCer, α-C-GalCer, —OCH, GSL-1, and iGB3.

In various embodiments, certain cells may be activated and/or stimulated with the present aAPCs. In various embodiments, the present aAPCs prevent the induction of anergy. Such processes may occur in vivo to stimulate a patient's immune response or ex vivo to establish a therapeutically effective amount of cells that are useful for immunotherapy upon re-introduction into a patient. In some embodiments, the cells of the present invention are T cells or T lymphocytes. These cells belong to a group of white blood cells known as lymphocytes and play a central role in cell-mediated immunity. Different types of T cells are encompassed by the present invention, including, but not limited to, T helper cells, cytotoxic T cells, memory T cells, regulatory T cells (also known as suppressor cells), and Natural Killer T cells. A T cell can be distinguished from other lymphocytes by the presence of a T cell receptor (TCR) on its cell surface. A T cell receptor is a protein that is found on the surface of a T cell and it is responsible for recognizing antigens bound to MHC molecules.

In some embodiments, the cells of the present invention are Natural killer T (NKT) cells. NKT cells are a rare subset of T cells that display molecules characteristic of both natural killer (NK) and T cells. Circulating numbers of NKT cells are markedly decreased in patients with melanoma, prostate cancer, chronic myelogenous leukemia, malignant lymphoma, and numerous other cancers. Furthermore, it has been recently shown that NKT cells can both directly and indirectly mediate anti-tumor immunity. In fact, in vivo activation of these cells through treatment with a synthetic glycolipid is currently being used in clinical trials. However, it is thought that their anti-tumor effects are hampered because both the number and functional activity of NKT cells is reduced in cancer patients. Thus, in some embodiments, the invention involves ex vivo expanded effector NKT cells, rather than direct in vivo NKT cell activation. To date, immunotherapy utilizing the NKT/CD1d system has been limited by the use of α-GalCer pulsed autologous DC or by direct injection of α-GalCer. Consequently, the present inventors have developed CD1d- (e.g., CD1d-Ig) based artificial Antigen Presenting Cells (aAPC) for the modulation of NKT cells. These CD1d-based aAPC facilitate the growth of primary NKT cells. In some embodiments, the adoptive transfer of ex vivo generated NKT cells can be an effective immunotherapeutic strategy against various diseases, including various cancers. In other embodiments, the CD1d-based aAPCs are directly administered to patients to expand NKT cell populations in vivo.

In some embodiments, the present invention relates to expansion of Type I NKT cells (also known as invariant or semi-invariant NKT cells—iNKT), which express an invariant Vα14Jα18 TCR in mice and Vα24Jα18 TCR in humans. In some embodiments, the present invention relates to expansion of Type II NKT cells, which are CD1d restricted T cells that express a more diverse set of α chains in their TCR and recognize different lipid antigens. It is thought that type I NKT cells exert potent anti-tumor effects, whereas type II NKT cells generally suppress tumor immunity through the production of IL-4 and IL-13. Type I NKT cells are further classified based on their expression of classic TCR cell surface markers. In some embodiments, the present invention relates to preferential expansion of Type I NKT cells over Type II NKT cells. These subsets have distinct Th1 and Th2 cytokine profiles. $CD4^+$ NKT cells produce Th1 and Th2 cytokines, whereas the $CD4^-$ subset, which includes both $CD8^+$ & DN, primarily produce Th1 cytokines. The majority of human NKT cells express CD161, CD56 as well as NKG2D. Interestingly, NKT cells are phenotypically similar to effector T cells because they express non-lymphoid tissue homing chemokine receptors such as CCR2, CCR5, and CXCR3. Given that NKT cells can rapidly produce Th1, Th2, and Th17-type cytokines, and activate cells of both the innate and adaptive immune systems, they are thought to be important modulators of the immune response.

In some aspects, the invention provides a method for preparing an antigen-specific NKT population for adoptive transfer. The method comprises providing a sample comprising NKT cells from a patient, where the patient is in need of adoptive transfer of antigen-specific NKT cells. The NKT cells, or sample containing the NKT cells, are contacted with a population of aAPCs as described in detail herein, each of which presents an antigen (e.g. a lipid or glycolipid) of interest, e.g. in the context of CD1d, and thereby binds antigen-specific NKT cells in the sample. In some embodiments, the lipid antigen is one or more of α-GalCer, α-C-GalCer, -OCH, GSL-1, and iGB3. α-GalCer, the best characterized stimulator of NKT cells is a potent inducer of stimulation and expansion, but secondary challenges in vivo renders NKT cells anergic. iGb3, has not been as well characterized; however it has been shown to develop murine NKT cells. Moreover, it has been shown to expand NKT cell populations at levels similar to treatment with α-GalCer. Additionally, iGb3 has a lower affinity with different activation kinetics.

In some embodiments, NKT cells are stimulated in culture with the presence of a feeder cell system, such as a feeder cell system that supports differentiation of hematopoietic stem cells. In some embodiments, the feeder cell system is OP9-DL1.

In various embodiments, the present aAPCs provide for about 100-10,000 fold expansion (or more) of NKT cells (e.g. about 100, or about 300, or about 500, or about 700, or about 1000, or about 2000, or about 3000, or about 4000, or about 5000, or about 7500, or about 10000 fold expansion) in the span of, for example, less than about one month, or less than about three weeks, or less than about two weeks. The resulting cells can be administered to the patient to treat disease. The aAPC may be administered to the patient along with the resulting antigen-specific T cell preparation in some embodiments.

One hallmark of NKT cells is their ability to produce large amounts of Th1 and Th2 cytokines, within hours after activation. Accordingly, in some embodiments, the present aAPCs stimulate the production of Th1 and Th2 cytokines. Further the present aAPCs can induce NKT cells to undergo clonal expansion. Further the present aAPCs can induce NKT cells to activate one or more of NK cells, neutrophils, macrophages, dendritic cells (DC), B cells, and T cells. Moreover, the activated NKT cells of the present invention can induce cell death in tumor cells by the expression of a large array of cell death-inducing effector molecules, including perforin, FAS ligand, and TNF-related apoptosis inducing ligand (TRAIL), like other cytotoxic cells, such as NK cells and CTL.

The potential to manipulate NKT cells for therapeutic purposes has markedly increased with the ability to stimulate and expand human NKT cells using α-GalCer and a milieu of cytokines. However, since CD4+NKT cells have been shown to suppress anti-tumor responses in mice and humans, it is possible that nonselective activation of all NKT cells (i.e. global stimulation with α-GalCer) or activation of the wrong subset could result in unwanted immunological outcomes. Accordingly, the present aAPCs provide, in some embodiments, activation of specific subtypes of NKT cells, including those that provide therapeutic outcomes. In some embodiments, the NKT cell subset is CD4+, CD8+ or CD4−CD8−. In addition, there are distinct Th1 and Th2 cytokine profiles of these subsets. CD4+ NKT cells produce Th1 and Th2 cytokines, whereas the CD4− subset, which includes both CD8+ and DN, primarily produce Th1 cytokines (Table 1).

TABLE 1

Phenotypic comparison of human Vα24i NKT cell subsets [a]

| Vα24i NKT cell subsets (CD1d-restricted) | Effector function (polarization, production of cytokines and cytotoxic molecules) | Chemoattractant receptors expressed[b5] | Adhesion molecules expressed | NK receptors expressed |
|---|---|---|---|---|
| CD4+ Vα24i NKT | Th1 and Th2 IL-10 IL-2 GM-CSF TNF-α Some express: CD95Le | CCR1 (~15%) CCR2 (~75%) CCR4 (~30%) CCR5 (~75%) CCR7 (~20%) CXCR3 (>90%) CXCR4 (~100%) | CD49a (~20%) CD62L (~20%) CLA (5-10%) α4β7 (~65%) | CD161 |
| CD4− Vα24i NKT | Th1 TNF-α Some | CCR1 (~60%) CCR2 (~90%) CCR5 (~90%) | CLA (5-15%) α4β7 | CD161 2B4 CD94 |
| (CD8+ & CD4−CD8−) | express: Perforin | CCR6 (~80%) CCR7 (~20%) CXCR3 (>90%) CXCR4 (~100%) CXCR6 (~85%) | (~75%) CD11ahigh | NKG2A NKG2D |

[a] The data in this table is representative of freshly isolated PBMC
[b] The numbers in parentheses represent percent positive cells for the specific receptor. Characteristic receptors for each subpopulation are indicated in boldface type.

Further, the present invention relates, in some embodiments, to NKT cells classified as NKT1 and NKT2, respectively. In some embodiments, the NKT cells express one or more of CD62L, CD94, CD28, CD56, and CD161. In some embodiments, the NKT cells are phenotypically similar to effector T cells because they express non-lymphoid tissue homing chemokine receptors such as CCR2, CCR5, and CXCR3 (Table 1).

Severely diminished immune responses can result from viral infection, myeloablative conditioning regimens, or systemic malignancy. Adoptive immunotherapy is one strategy used to enhance anti-tumor immune responses in cancer patients, and it can restore early post-transplantation immune competence in allogeneic hematopoietic stem cell (HSC) transplant recipients. Adoptive immunotherapy involves stimulation of T cells, ex vivo, followed by transfer of expanded numbers of activated autologous T cells back into patients. In some embodiments, the present methods comprise the use of the described aAPCs in adoptive immunotherapy approaches. Autologous tumor-specific cells can directly induce tumor shrinkage in vivo but a limitation of this approach is that patients must have preexisting tumor-reactive cells, and these are difficult to identify in non-melanoma malignancies. To overcome this limitation, T cell receptor (TCR) gene transfer or chimeric antigen receptors can be utilized in the present methods or with the present aAPCs. It has been hypothesized that the effectiveness of TCR gene transfer of T cells is reduced, at least in part due to the pairing of the newly introduced TCR α and β chains with the endogenous TCR proteins. Thus, two groups have reported that transducing TCR genes into HSC, which can be differentiated into functional T cells, and results in the generation of large numbers of mature, antigen-specific T cells from undifferentiated hematopoietic progenitors. While these TCR transduction strategies have been shown to be useful for providing tumor-specific responses, the utilization of adoptive immunotherapy with invariant natural killer T (NKT) cells (or Type I NKT cells) as described herein (e.g. as expanded with the methods described herein) would be advantageous because one could elicit, for example, both anti-tumor and anti-viral immune responses. Unlike MHC-restricted T cells, NKT cells acquire their effector functions during development, and their activation, following recognition of antigen presented in the context of CD1d molecules, results in rapid production of large amounts of cytokines. NKT cell-mediated cytokine production, for instance as stimulated by the present aAPCs leads to induction of both the innate and adaptive immune responses. Despite the importance of NKT cells in regulating immune responses, their low frequency significantly restricts their potential for clinical application. The inventors have shown that functionally mature human NKT cells can be generated in vitro from hematopoietic stem progenitor cells (HSPC). Accordingly, the present aAPCs may be used in methods to generate mature NKT cells from HSPCs, in vivo or in vitro. In some embodiments, the present aAPCs may be used to generate functional NKT cells from stem progenitor cells of patients with hematological malignancies. In various embodiments, adoptive transfer of HSPC-generated human NKT cells can lead to tumor regression and enhance antiviral responses in patients with hematological malignancies.

In some embodiments, the invention involves expansion of NKT cells in vivo or ex vivo for treatment of an infectious disease, including viral, bacterial, or parasitic infections.

Generally, NKT cell numbers are lower in cancer patients as compared to age and gender matched healthy controls Circulating numbers of NKT cells are reduced in, for example, patients with advanced prostate cancer, melanoma, myelodysplastic syndromes, and progressive malignant myeloma. Furthermore, even after effective removal of the tumor by surgery or radiotherapy, NKT cell numbers are often not restored to a normal level.

In some embodiments, the present aAPCs, or cells stimulated therewith (e.g. in vivo or ex vivo) are useful in the treatment of cancer.

In some embodiments, the cancers may include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the cancer is one or more of prostate cancer, melanoma, myelodysplastic syndromes, and myeloma.

In various embodiments, the cancer is stage I, stage II, stage III, or stage IV. In some embodiments, the cancer is metastatic and/or recurrent.

Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In some embodiments, the aAPCs or activated cells of the present invention are used as an adjuvant therapy in the treatment of a cancer. In some embodiments, the aAPCs or activated cells of the present invention are used as the sole adjuvant therapy in the treatment of a cancer.

In some embodiments the aAPCs or activated cells of the present invention are administered as a neoadjuvant therapy prior to resection. In certain embodiments, neoadjuvant therapy refers to therapy to shrink and/or downgrade the tumor prior to any surgery. In some embodiments, neoadjuvant therapy means an aAPCs or activated cell of the present invention is administered to cancer patients prior to surgery. Types of cancers for which neoadjuvant chemotherapy is commonly considered include, for example, breast, colorectal, ovarian, cervical, bladder, and lung.

In some embodiment, the patient has an autoimmune condition or infectious disease for which NKT cells can play a role in mitigation.

Provided herein is a method for modulating T cell function using artificial antigen presenting cells, including but not limited to Natural Killer T Cells. Artificial Antigen Presenting Cells (aAPC) can modulate the function of NKT cells. For example, quantum dot based-artificial antigen presenting complexes can be used to specifically stimulate NKT cells. These complexes can be loaded with monomeric antibodies and dimeric fusion proteins and used to activate both NKT cells hybridomas and primary NKT cells. One method of modulating NKT cells in patients is by adoptive transfer of ex vivo generated NKT cells as an immunotherapeutic modality, whereby stimulation of tumor specific T cells leads to their ex vivo expansion, followed by transfer of these expanded autologous T cells back into patients. Another embodiment includes adoptive transfer mediated generation of NKT cells and antigen specific CTLs from adult stem progenitor cells.

aAPCs can be used to modulate NKT cells both in vitro, in vivo, and ex vivo. For in vitro studies, nanoparticle based aAPC can be used to label or stain NKT cells for detection by flow cytometry, immunohistochemistry, or fluorescent microscopy. These aAPC can also be used in vitro to assess the co-stimulatory requirements for NKT cell proliferation and activation by use in combination with proliferations assays (WST-1, $^3$H thymidine incorporation, CSFE). In vivo aAPC can be used to activate or inhibit NKT cells depending on the disease context. In the context of most cancers and infections NKT cells can be activated by aAPC loaded with lipid antigens such as α-GalCer or α-c-GalCer, for autoimmune diseases NKT cells can be activated with aAPC loaded with -OCH as a form of treatment, and when NKT cells are aberrantly activated in some pathological conditions such as allergic asthma or psoriasis, aAPC loaded with inhibitory lipids such as GD3 or GM3 can be used block NKT cell function. Ex vivo aAPC can be used to expand or propagate NKT cells in culture to be given back as an adoptive immunotherapeutic strategy either directly from peripheral blood or generated from stem progenitor cells (CD34+) by using aAPC in combination with stromal culture systems.

The aAPC may be administering by a number of routes including, but not limited to: parenteral, enteral, and topical, such as intravenous, intraperitoneal, intramuscular, or subcutaneous, to a mucosal surface (oral, sublingual or buccal, nasal, rectal, vaginal, pulmonary), or transdermal. For example, nanosized quantum dot-based aAPCs may be administered intranasally to a patient in need of NKT cell generation and/or expansion in vivo.

In some embodiments, the invention provides kits that can simplify the administration of any agent described herein. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

Figure 12:
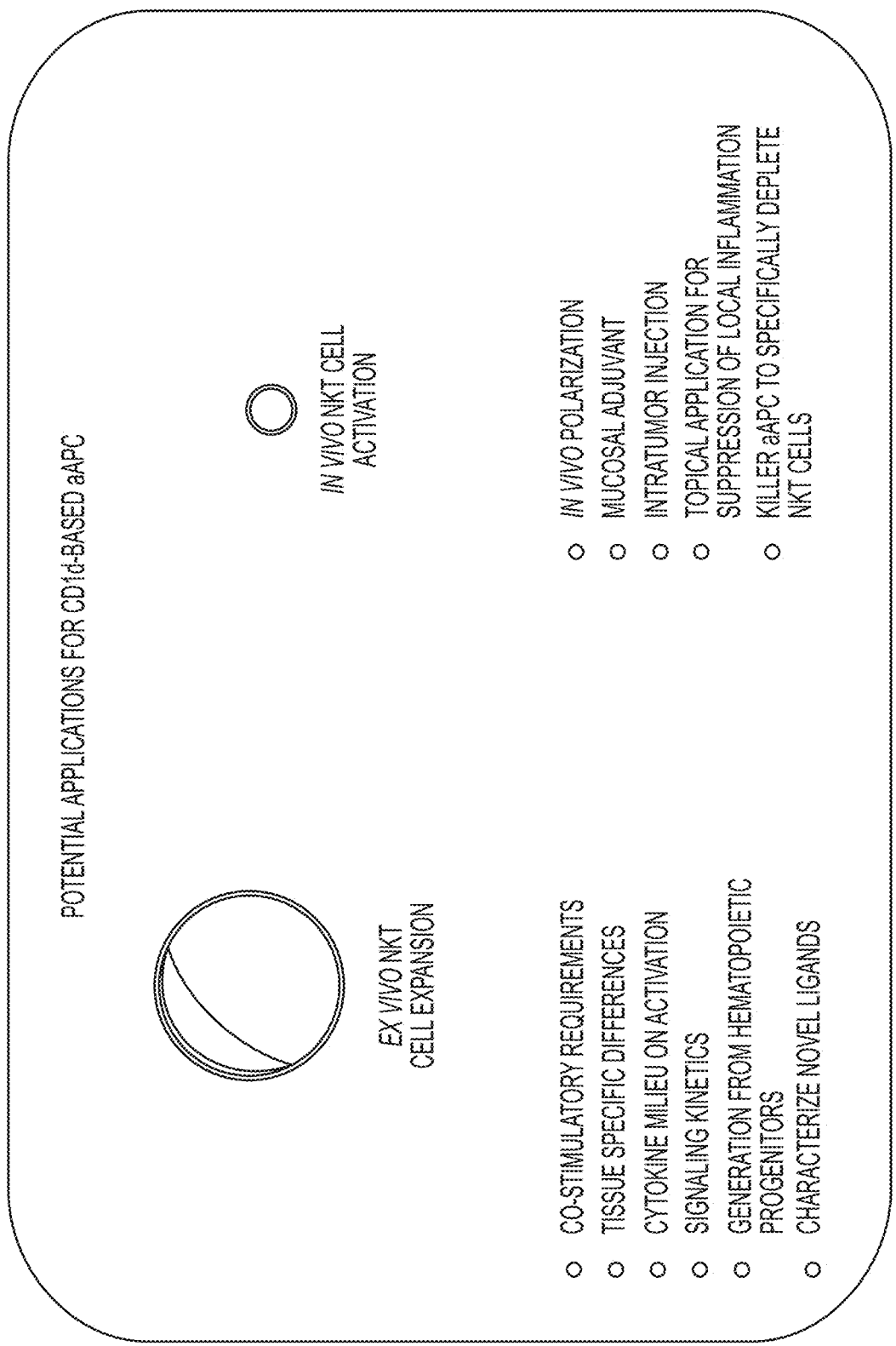
FIG. 12 shows illustrative utilizations of CD1d-based aAPC mediated activation of NKT cells as a broad-based platform. CD1d-Ig based aAPC is a unique system that can be used to characterize the requirements for NKT cell activation and proliferation both in vitro and in vivo. Given the feasibility and reproducibility of this system, it can help us connect the dots and assess the costimulatory requirements and tissue specific differences in specific NKT cell subsets. In addition, NKT cells can be cultured with aAPC in the presence of certain cytokines or putative ligands and following activation their downstream signaling kinetics can be determined. aAPC can be used to activate and expand NKT cells from humans as well different species of animals. Ongoing studies are focused on comparing different matrices for optimal in vivo use. Then one could potentially use the CD1d-Ig based aAPC to polarize NKT cell cytokine profiles in vivo and examine their efficacy in vaccination strategies to either enhance NKT cell activation or specifically deplete undesired NKT cell responses.

FIG. 12 shows illustrative utilizations of CD1d-based aAPC mediated activation of NKT cells as a broad based platform.

This invention is further illustrated by the following non-limiting examples.

EXAMPLES

Methods for Making Artificial Antigen Presenting Cells

Provided herein is a method for preparing artificial antigen presenting cells that can be used to modulate NKT activity. The following example illustrates a method of preparing artificial antigen presenting cells.

Example of Preparation of CD1d-Based aAPC

Generation of aAPC 1.1) Before adding proteins to beads, prepare all reagents and buffers: 0.1M Borate buffer; 1×D-PBS (no $Ca^{2+}$ and $Mg^{2+}$); Bead Wash Buffer (1×PBS+5% Human AB serum+0.02% sodium azide); Complete medium (RPMI medium+100 mM sodium pyruvate, 10 mM non-essential vitamin solution, 100 mM MEM Vitamin solution, 1% 2-mercaptoethanol, 10 µM ciprofloxacin, 5% Human AB serum); MACS buffer (1 L PBS free of $Ca^{2+}$ and $Mg^{2+}$, 5 g BSA, and 2 mmol EDTA).

1.2) Rinse 1 ml Dynabeads® M-450 Epoxy beads with 3 ml sterile 0.1 M Borate buffer (boric acid and water, pH 7.0-7.4) in a 5 ml clear borosilicate glass threaded vial.

1.3) In a separate 1.5 ml microcentrifuge tube, add 100 µg hCD1d-Ig dimer and 20 µg costimulatory molecules (example: anti-CD28mAb) to 1 ml PBS w/o $Ca^{2+}$ or $Mg^{2+}$.

1.4) Place bead containing glass vial on magnet and aspirate borate buffer from beads. Add protein mixture from step 1.2 to glass vial and replace cap. Mix immediately by inverting the vial, cover the cap with parafilm, and place on a rotator and incubate overnight at 4° C.

1.5) The next day, place glass vial on magnet and remove protein mixture, while carefully avoiding beads. Wash the beads by adding 3 ml bead wash buffer (PBS with 5% AB serum+0.02% sodium azide), and incubating at 4° C. on a rotator for 5 min. Repeat twice.

1.6) Beads can be stored in this bead wash mixture. To make functional aAPC, remove a small aliquot and count the beads using a hemacytometer. Check that the proteins are stably loaded onto the beads by staining with antibodies (ex. PE-conjugated anti-mouse IgG1) and performing flow cytometric analyses.

1.7) To load beads with antigen, remove $5 \times 10^7$ beads, and add to a small 1.5 ml glass vial, rinse beads with 1 ml sterile PBS. Resuspend washed beads with 1 ml sterile PBS and add antigen; example: Load with α-GalCer (5 µg/ml).

Isolation of $CD161^+CD3^+$ cells.

2.1) Collect peripheral blood mononuclear cells (PBMC). For Ficoll density gradient centrifugation separation of lymphocytes from a buffy coat or leukopheresis pack, first dilute heparinized blood with an equal volume of 1×PBS at room temperature.

2.2) Add 15 ml of Ficoll (warmed to room temperature) to 50 ml conical tubes. Slowly overlay 25 ml of the diluted blood mixture on top of the Ficoll. Centrifuge at 2000 rpm for 30 min at room temperature with the brake off.

2.3) Carefully remove the lymphocyte interface (white ring between the media and Ficoll) with a Pasteur pipette and transfer to a new 50 ml conical tube.

2.4) Wash the cells by filling up the tube to 50 ml with PBS and centrifuging at 1500 rpm for 5 min. Discard the supernatant and combine the tubes from a single individual to a single tube and wash the peripheral blood mononuclear cells (PBMC) again with 20 ml PBS. Then count the PBMC and resuspend at a concentration of $5 \times 10^7$ cells/ml in MACS buffer (1 L PBS free of $Ca^{2+}$ and $Mg^{2+}$, 5 g BSA, and 2 mmol EDTA).

2.5) In order to isolate the T cell fraction, start with 2 ml of PBMC ($10^8$ cells) and add 100 µL of Pan T cell enrichment solution from the EASYSEP Human T Cell Enrichment Kit. Incubate at room temperature for 10 min.

2.6) Add 100 µL of magnetic particles to the solution and incubate at room temperature for another 10 min. Bring the final volume of solvent to 2.5 ml and place the tube in the purple magnet for 5 min. Quickly pour off the $CD3^+$ fraction into a 15 ml conical tube.

2.7) Wash the cells by adding 5 ml cold MACS buffer, count the number of viable cells, and remove an aliquot for FACS staining.

2.8) To select the $CD161^+$ cells, first resuspend enriched T cells in 980 µl ice cold MACS buffer, add 10 µg anti CD161 mAb, and incubate in refrigerator for 10 min.

2.9) Centrifuge the cells at 1500 rpm at 4° C. for 5 min. Then reconstitute the cell pellet in 800 µL of MACS buffer. Add 200 µL of anti-mouse IgG1 microbeads and incubate the solution for 10 min at 4° C.

2.10) During this incubation step, equilibrate a LS column by adding 3 ml MACS buffer.

2.11) Next, wash the cells by centrifuging 1500 rpm at 4° C. for 5 min. Resuspend the cells in 3 ml MACS buffer. Then pipette the cells into the LS MACS separating column. Make sure to avoid generating bubbles by pipetting slowly. Rinse the column by adding 3 ml of MACS buffer. Repeat twice.

2.12) Add 3 ml fresh MACS buffer and remove column from magnet. Place column into a 15 ml conical tube. Insert plunger and push out contents to obtain purified $CD161^+CD3^+$ cells. Count NKT cell enriched fraction. You should have 2-4 million cells.

aAPC-mediated NKT cell expansion 3.1) Set up co-culture by adding $10^6$ enriched $CD161^+$ $CD3^+$ T cells and $10^6$ aAPC in 16 ml complete medium (complete medium+IL-2, 100 U/ml). Plate this mixture by adding 160 μl/well final volume to a 96 well tissue-culture treated polystyrene, U-bottom plate with low-evaporation lid. Perform medium exchange every 7th day by adding 80 μl of fresh medium.

3.2) Harvest cells, count, and perform FACS staining on day 12-14.

Functional test: aAPC-mediated stimulation of NKT cells 4.1) Set up $5 \times 10^4$ NKT cells/well with $5 \times 10^5$ aAPC in 200 μl final volume (complete medium) in 96 well U-bottom plate.

4.2) Harvest cell culture supernatant for ELISA after 24-48 hr.

Figure 2:
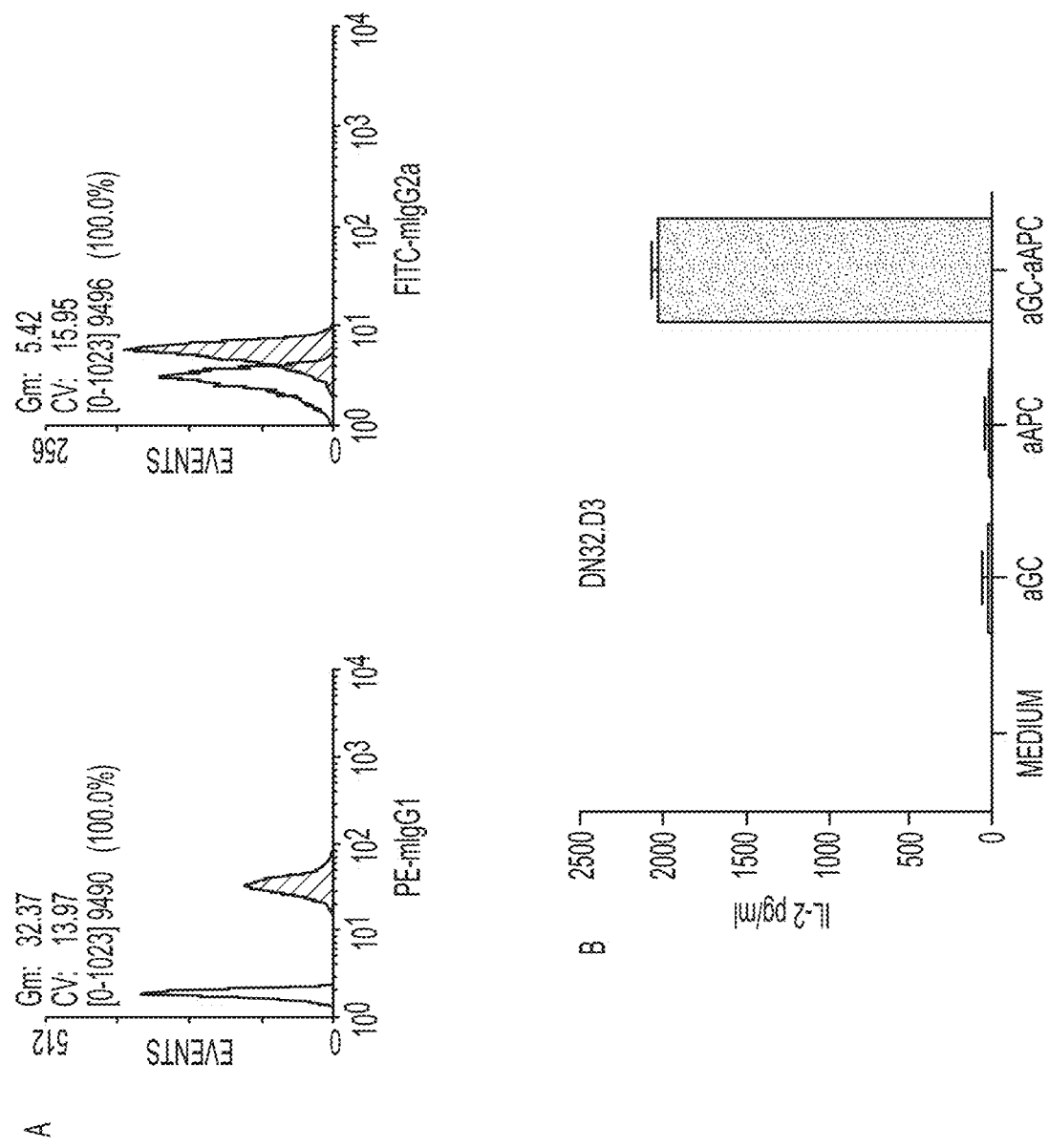
FIG. 2 shows FACS staining of surface proteins on aAPCs. Panel A shows aAPCs were tested for the presence of CD1d:IgG dimer (via staining with PE-conjugated anti-mouse IgG1) as well as anti-CD28 antibody (using FITC-conjugated anti-mouse IgG2a). Open histograms indicate isotype control; filled histograms represent the indicated antibodies. CD1d-Ig Expressing aAPC can Stimulate IL-2 Production by NKT cells. B) The Vα14+ mouse NKT cell hybridoma, DN32.D3, was co-cultured with either medium, soluble antigen (α-GalCer), unloaded aAPC or α-GalCer-loaded aAPC. Culture supernatants were harvested and standard sandwich ELISA was used to measure IL-2 production.
Figure 3:
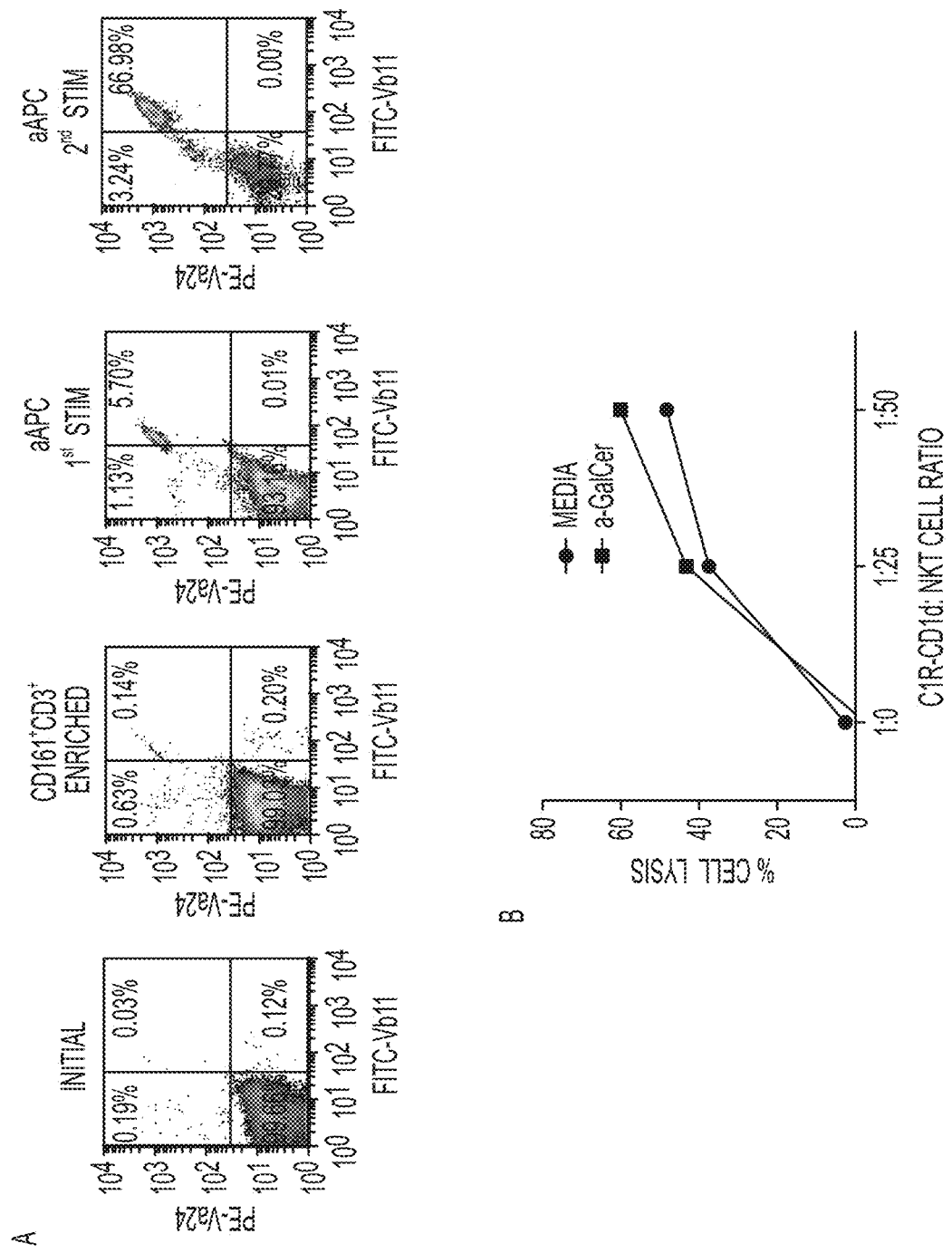
FIG. 3 shows expansion of NKT cells by CD1d-Ig coated artificial antigen presenting cells. Panel A shows primary $CD3^+CD161^+$ double positive cells were isolated from PBMCs using magnetic separation. The sorted cells were stimulated with α-GalCer loaded, CD1d-Ig coated aAPC for 14 days. The cells were stained for Vα24 and Vβ11 following aAPC stimulation.

This example shows a method for generating a CD1d-Ig based aAPC, made by covalent coupling of CD1d-Ig and anti-CD28 mAb to magnetic beads to stimulate NKT cells as a standardized method for the propagation of NKT cells (FIG. 1). First, one must demonstrate that the CD1d-Ig fusion proteins are stably immobilized onto the surface of the magnetic beads. As shown in FIG. 2, panel A, CD1d-Ig and anti-CD28 antibodies were both expressed on the surface of the magnetic beads. To examine the stimulatory capacity of the aAPC, NKT cell hybridomas were co-cultured with aAPC overnight, the culture supernatants were harvested and IL-2 production was measured by ELISA. CD1d-Ig based aAPC were able to stimulate the NKT cell hybridomas at levels equal to or higher than their cellular counterparts (FIG. 3, data not shown). The mouse NKT cell hybridomas are stimulated by human CD1d-based aAPC (FIG. 2, panel B), which provides a simple method for testing each batch of aAPC.

Figure 4:
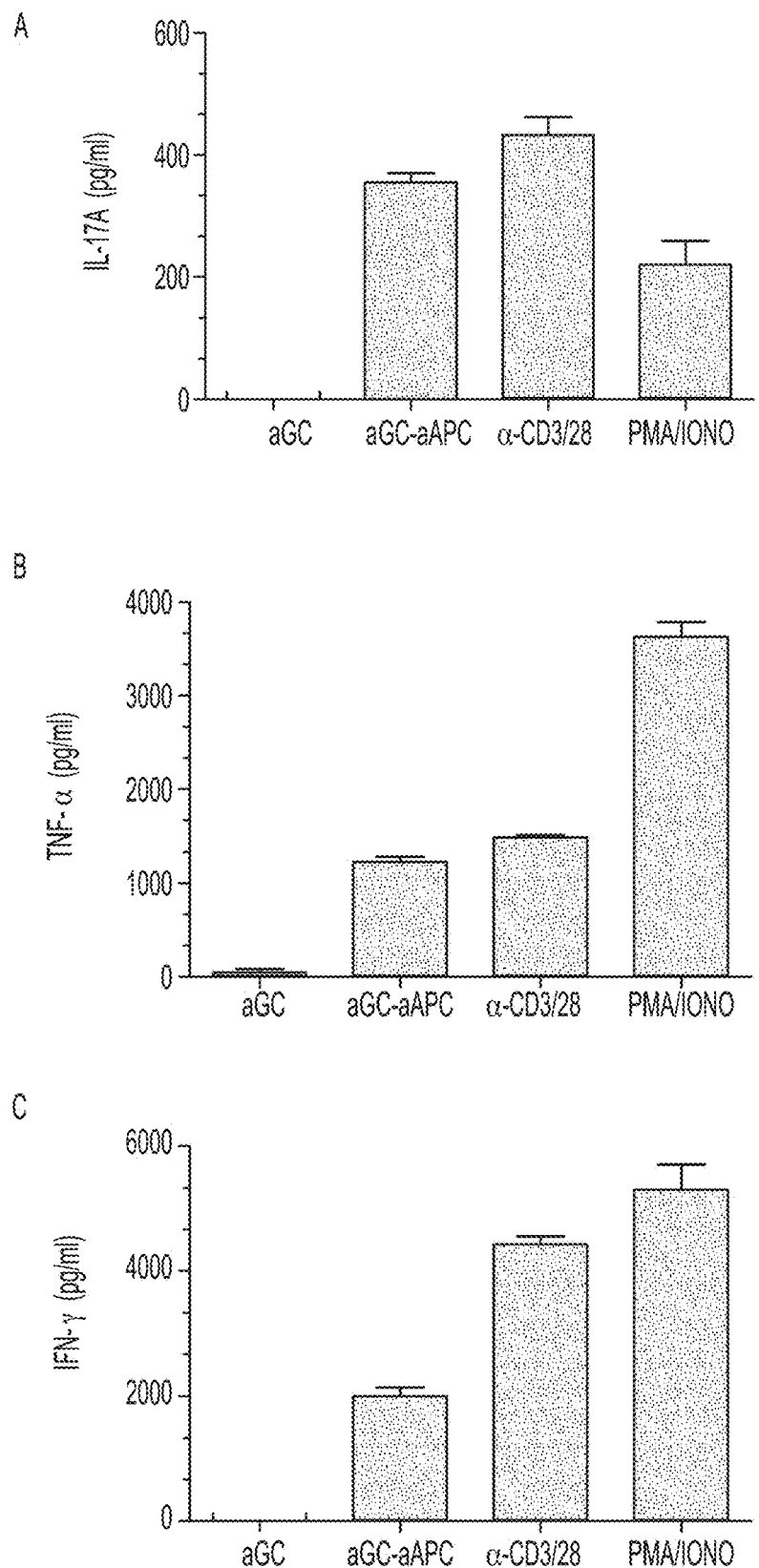
FIG. 4 shows cytokine profiles of aAPC-expanded NKT cells. After stimulation with a GalCer loaded aAPC for two weeks, the expanded NKT cells ($1 \times 10^5$/well) were cocultured with soluble α-GalCer, PMA/Ionomycin, anti-CD3/28 microbeads, or α-GalCer loaded aAPC ($2 \times 10^5$/well) for 48 hr. (A) IL-17A, (B) TNF-α, and (C) IFN-γ production was measured by standard cytokine ELISA. Data shown are net cytokine production after subtracting the negative controls (media and empty beads).
Figure 4:
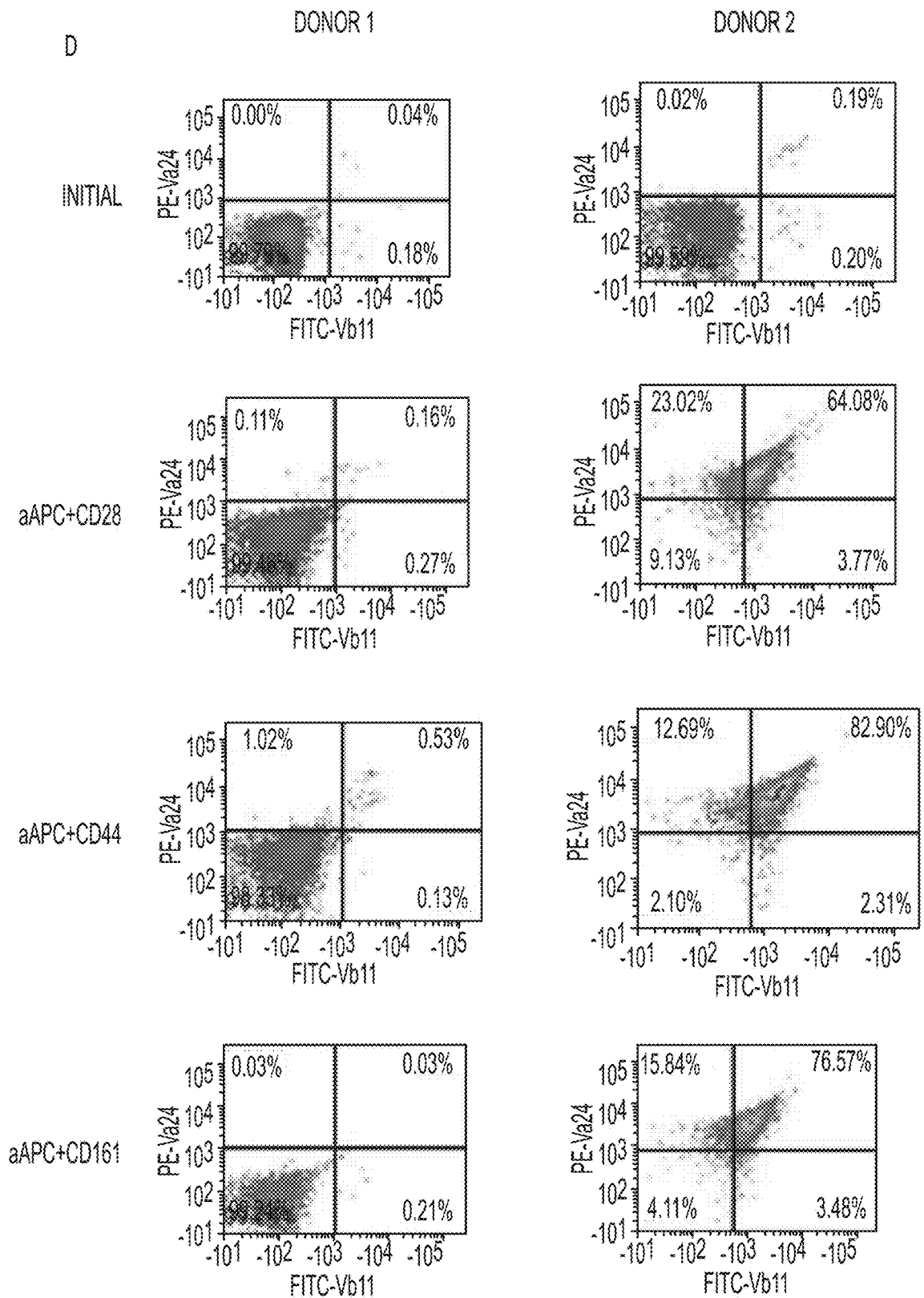

The propagation potential of aAPC was next studied. Thus human T cells were isolated from the peripheral blood. First the CD161$^+$CD3$^+$ T cell fraction was enriched by magnetic bead separation. Then, the T cells were stimulated biweekly with α-GalCer-loaded aAPC. Importantly, it was shown that even with a relatively low initial NKT cell population (0.03%), it was possible to expand the cells to ~67% Vα24$^+$Vα11$^+$ (FIG. 3). NKT cells from the PBMC of many healthy volunteers and cancer patients have been expanded. α-GalCer loaded aAPC were able to expand the NKT cells population in both groups. Notably, the expansion rate was highly donor dependent. As expected, the higher the initial population of Vα24$^+$ cells, the greater the percentage of expansion. In addition, when using a starting population of 2 million cells CD161$^+$CD3$^+$T cells, one can obtain >10$^7$ cells after two rounds of expansion. Therefore, these expanded NKT cells can be used for functional studies as shown in FIG. 4. The ex vivo expanded NKT cells remain responsive to α-GalCer stimulation and are potent producers of IL-17A, TNF-α, and IFN-γ. Collectively, these data show, among others, that CD1d based-aAPC can be used to effectively expand and stimulate primary human NKT cells.

adoptive immunotherapy. Here, it was demonstrated that CD1d-Ig based aAPC can be used to expand functional NKT cells. This aAPC expansion method provides a simple and reliable method for expanding and enriching human NKT cells. Our aAPC can be modified to systematically evaluate the role of a panel of potential costimulatory molecules and assess their role on NKT cell proliferation and function. Thus, aAPC represent a robust versatile technology useful for inducing and expanding NKT cells. The generation of aAPCs takes less than one week and is suitable for the production of large quantities of beads. However, a critical step in generating the aAPC is to confirm that CD1d-Ig is stably immobilized on the surface of the beads and to assess their functionality to ensure consistency from batch to batch. One may phenotypically and functionally characterize the aAPC-expanded NKT cell population. As shown in FIG. 4, stimulation with α-GalCer-loaded aAPC expressing anti-CD28 can result in NKT cells producing Th1, Th2, and Th17 type cytokines. Murine studies have reported that challenge with IL-33, a recently identified cytokine, resulted in increased levels of circulating inflammatory cytokines such as IL-5 and IL-13. Treatment of NKT cells with IL-33 enhanced their cytokine production (J Immunol 172, 5304-5312 (2004)). IL-33 is a specific ligand for ST2 and it has been shown that soluble ST2 can block IL-33 signaling. Thus, as an example of a future application, aAPC expressing ST2 could be generated and used to determine if one could selectively inhibit the production of Th2 cytokines while inducing Th1 cytokines secretion by NKT cells. It has also been reported that i.v. injection of Kb-expressing aAPC into C57BL16 mice resulted in decreased lung metastasis of tumor (*Cancer Res* 69, 9376-9384 (2009)). Importantly, these data demonstrate that aAPC traffic to the lung and are able to activate effector T cell subsets. Therefore, one could generate multiple types of aAPC and examine the interplay between antigen specific T cell subsets. To summarize, these studies demonstrate the potential uses of CD1d-Ig based aAPC to replace normal cellular APC and have to the potential to enhance current clinical approaches for NKT cell based-adoptive immunotherapy.

Adoptive Transfer of Ex Vivo Generated NKT Cells as an Immunotherapeutic Modality.

Ex vivo expanded NKT cells can be used for cancer immunotherapy. However, rather than using the entire expanded population, the best effector subset should be first defined. Further, adoptive transfer of an additional effector population such as antigen specific CTL may be effective. This example, in part, is directed to utilizing the CD1d-Ig based aAPC to identify the most effective NKT cell subset and evaluate its role in tumor immunotherapy.

Innovations in molecular design have made it possible to construct soluble multivalent MHC complexes, including

TABLE 1 aAPC induced NKT cell expansion*

|  | EXP1 | EXP2 | EXP3 | EXP4 | EXP5 | EXP6 |
|---|---|---|---|---|---|---|
| CD1d/28 | $8 \times 10^6$ | $7 \times 10^6$ | $8.7 \times 10^6$ | $7 \times 10^6$ | $2.8 \times 10^7$ | $1.4 \times 10^7$ |
| CD1d/44 | $7 \times 10^6$ | $1.4 \times 10^7$ | $5.3 \times 10^6$ | $7 \times 10^6$ | $1.4 \times 10^7$ | $1.1 \times 10^7$ |
| CD1d/161 | $3.5 \times 10^6$ | $1.0 \times 10^7$ | $7 \times 10^6$ | $1.1 \times 10^7$ | $1.4 \times 10^7$ | $1.1 \times 10^7$ |

*Data shown after 2 wk stimulation with beads, Initial cell number 2 ×10$^6$, after 2 wks The generation of a non-cellular aAPC is useful both for basic and translation research studies. aAPC can be used to study the basic requirements for NKT cell activation and it has clinical value for ex vivo expansion of NKT cells for MHC-Ig dimers and MHC tetramers, which have increased avidity for cognate T cell receptors and stably bind to antigen specific T cells. CD1d tetramers have permitted investigators to analyze the phenotype and function of particular subsets of Vα24+ NKT cells. However, MHC tetramers are formed by using biotinylated MHC complexes that are multimerized on an avidin scaffold and this approach employs a relatively rigid avidin-biotin based scaffold. Instead, here a general platform for presentation of soluble divalent MHC complexes using an Ig backbone as a molecular scaffold is described. The use of immunoglobulin as a molecular scaffold takes advantage of the flexibility of the Ig portion to optimize the overall avidity of binding.

Figure 5:
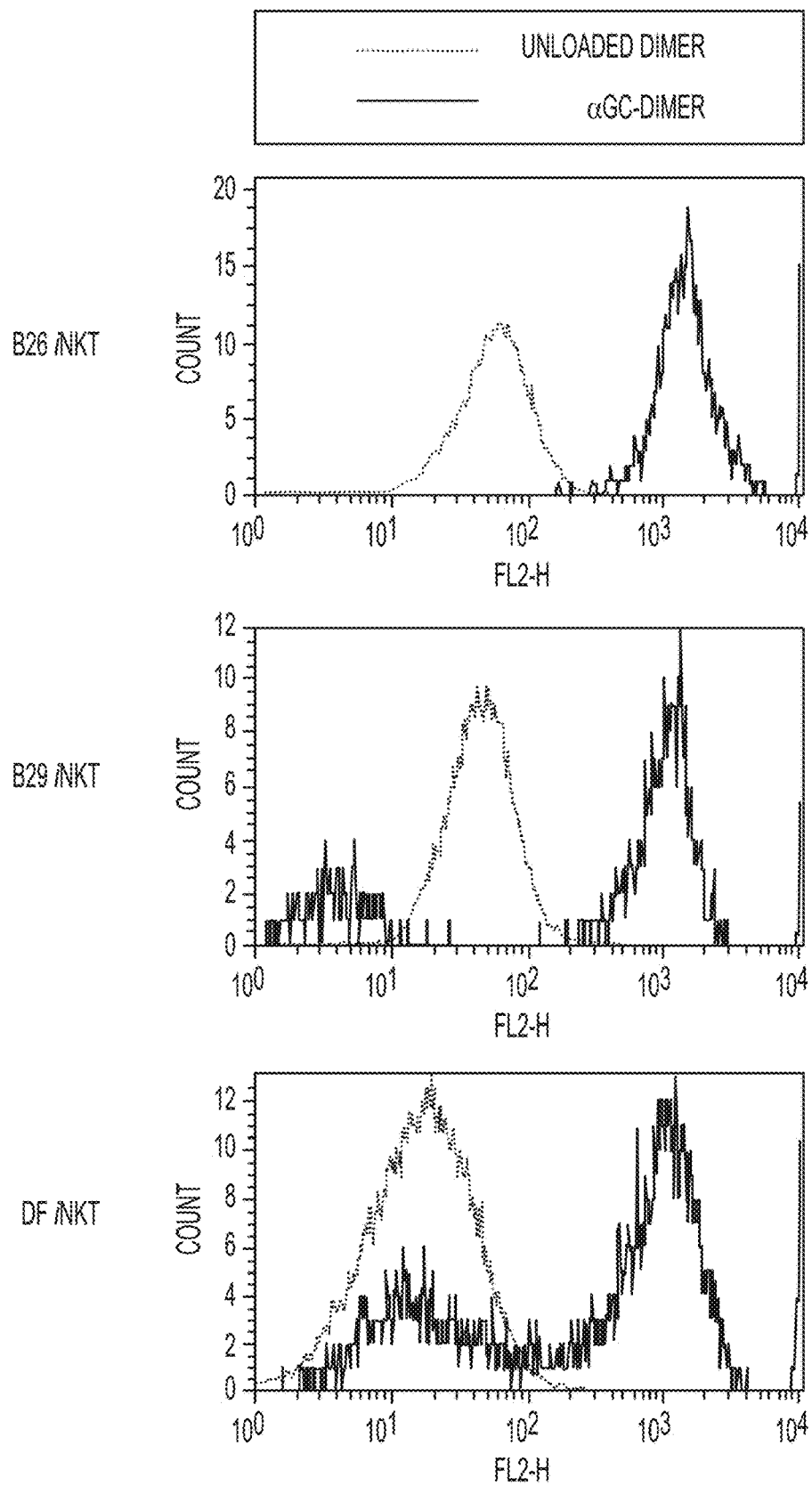
FIG. 5 shows CD1d-restricted NKT cells stained with α-GalCer-loaded CD1d1-Ig dimers. Recombinant soluble human dimeric CD1d-Ig (Pharmingen) was loaded with 40 molar excess aGalCer according to the manufacturer's instructions. In brief, lipids resuspended in PBS (pH 7.4) were mixed with the dimers and incubated at 37° C. overnight. Then the lipid-loaded CD1d dimers were incubated with PE-labeled anti-mouse IgG. Human NKT (Vα24) cell lines ($5 \times 10^5$) were stained with either empty or lipid-loaded CD1d-Ig dimers for 2 h at 4° C. and analyzed by FACS.
Figure 6:
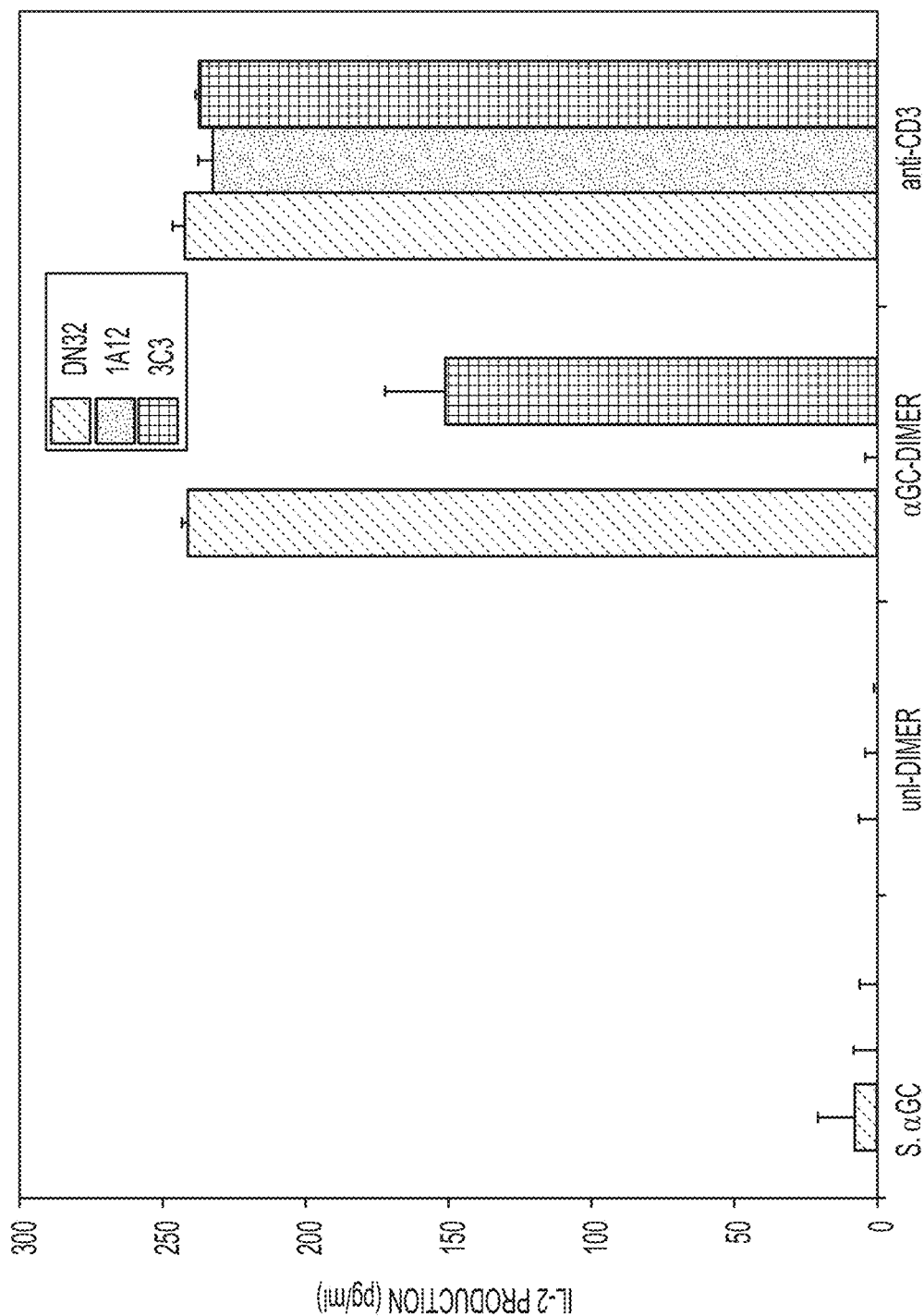
FIG. 6 shows that aGalCer-loaded CD1d1-Ig dimers can stimulate $V\alpha 14^+$ NKT cell hybridomas. Recombinant soluble murine dimeric CD1d-Ig was loaded with 40 molar excess aGalCer according to the manufacturer's instructions. Then the lipid-loaded CD1d dimers were diluted in PBS and used to coat 96-well flat bottom plates (1 µg/well). The plates were incubated at 37° C. for 2 hr and then washed extensively. NKT cell hybridomas, DN32.D3, N37-1A12, & N38-3C3 (referred to as DN32, 1A12 & 3C3) were incubated in the coated plate for 20-24 hr. Culture supernatants were harvested and standard sandwich ELISA was used to measure IL-2 production.

To assess the ability of α-GalCer loaded CD1d-Ig to bind to human NKT cells, CD1d-Ig fusion proteins were first loaded with α-GalCer. Then purified Vα24+Vβ11+ human NKT cell lines were stained with either unloaded or loaded CD1d-Ig molecules. As shown in FIG. 5, α-GalCer loaded CD1d-Ig molecules bind specifically to canonical NKT cell lines. It was next investigated whether these CD1d-Ig molecules could stimulate NKT cells. A panel of well-characterized murine NKT cell hybridomas was used to further study this system (murine NKT cell lines have been reported to recognize human CD1d molecules). Plates were coated with α-GalCer loaded CD1d-Ig molecules and the ability of these molecules to stimulate murine NKT cell lines was examined. α-GalCer only stimulated canonical Vα14+ NKT cell lines, but not the noncanonical, Vα5+ CD1d-specific cell line, 1A12. As a control, plate bound anti-CD3 was also used (FIG. 6). These data indicate, without wishing to be bound by theory, that all of these NKT cell lines can be stimulated non-specifically, but α-GalCer loaded CD1d-Ig molecules specifically stimulate only canonical, Vα14+ NKT cell lines, DN32 & 3C3. These data demonstrate that CD1d-Ig molecules specifically bind to and stimulate NKT cells.

MHC-Ig immobilized on aAPC is very potent and enables testing of many different culture conditions regarding antigen density and duration, aAPC to T cell ratio, as well as the ratio of Signal 1 to Signal 2. To evaluate if a CD1d-Ig based aAPC would have similar advantages, a CD1d-Ig based aAPC was generated by coupling CD1d-Ig onto magnetic beads. For an initial prototype, CD1d alone or in combination with anti-CD28 mAb was used (see FIG. 1, panel A for aAPC schematic). Next whether the CD1d1-Ig molecules were indeed stably immobilized onto the surface of the magnetic beads was evaluated. Thus the beads were stained with PE-labeled anti-mouse IgG1 antibodies and analyzed by flow cytometry. As shown in FIG. 2, panel A, it was found that CD1d-Ig and anti-CD28 antibodies were both expressed on the surface of the magnetic beads. Moreover, when the levels of CD1d in the presence and absence of anti-CD28 antibodies were examined there were no detectable differences in amount of CD1d-Ig bound (data not shown). Furthermore, CD1d expression was confirmed using anti-CD1d antibodies levels were similar to those detected with anti-mouse IgG1 (FIG. 2, panel A and data not shown).

Further studies sought to determine the stimulatory capacity of the aAPC. For these experiments the mouse NKT cell hybridomas that were utilized in FIG. 6 were used. As previously mentioned these cells have been well studied and are relatively easy to maintain. As a positive control a human B cell line transfected with CD1d, C1R-d was used, the murine NKT cell lines secreted IL-2 following stimulation with C1R-d and a phorbol ester. These data demonstrate that mouse NKT cell lines can be stimulated by human CD1d molecules. Next the NKT cell hybridomas were cultured with aAPC overnight, culture supernatants harvested, and measured IL-2 production was measured by ELISA. Importantly, it was found that CD1d-Ig based aAPC were able to stimulate the NKT cell hybridomas at levels equal to or higher than their cellular counterparts. Collectively these data suggest that utilizing CD1d1-Ig dimer technology can provide high affinity, divalent, and multivalent interactions that can trigger TCR crosslinking. These complexes, when properly immobilized can selectively stimulate effector NKT cells.

CD1d-Ig based aAPC can be used to stimulate NKT cell lines. To explore the potential of aAPC, T cells were stimulated with soluble antigen, aAPC, or irradiated PBMC once a week for two weeks. Remarkably, it was found that although the percentage of Vα24+T cells was very similar in cultures stimulated with α-GalCer-loaded aAPC or α-GalCer-pulsed irradiated PBMC, the actual cell number was much higher in the culture stimulated with α-GalCer-loaded aAPC. More importantly, it was found that the number of Vα24+NKT cells in all of the cultures containing APC was compared, the α-GalCer-loaded aAPC±anti CD28 induced significantly higher levels of proliferation compared to autologous α-GalCer pulsed PBMC.

Next, expansion NKT cells from PBMC from several healthy volunteers and cancer patients was attempted. As shown in Table 2 it was found that α-GalCer loaded aAPC were able to expand the NKT cells population in both groups. Notably, the percentage of NKT cells varied significantly in each individual, as has been reported in the literature. As expected the higher the initial population of Vα24+ cells, the greater the percentage of expansion. Significant expansion in the NKT cell population in PBMC isolated from an ovarian cancer patient using α-GalCer loaded aAPC is achieved. Thus these data demonstrate that CD1d-Ig based aAPC can be used to expand NKT cells from PBMC of cancer patients.

TABLE 2

Propagation of Human NKT cells from PBMC Of Healthy Volunteers and Cancer Patients using aAPC

| | | Initial Percent Positive (Vα14+) | Following αGalCer-aAPC stimulation |
|---|---|---|---|
| Healthy Controls | G002 | 0.53 | 7.83 |
| | NC5 | 0.16 | 5.56 |
| | NC10 | 0.01 | 0.09 |
| Cancer Patients | CP2 | 0.95 | 13.83 |
| | CP3 | <0.01 | 0.92 |
| | CP4 | <0.01 | 1.2 |

However, in agreement with the literature, some patients have barely detectable numbers of NKT cells. Consequently, it was tested whether PBMC from cancer patients were able to stimulate mouse NKT cell hybridomas at levels comparable to normal volunteers (data not shown). In this experiment, NKT cells were cocultured with PBMC from three normal controls and one breast cancer patient. Stimulation by murine thymocytes was used as a positive control. The normal controls were able to stimulate at least two of the four NKT cell hybridomas, however in this experiment PBMC from the breast cancer patient did not stimulate any of the NKT cells above background. Thus, these data suggest, without wishing to be bound by theory, that the low frequency of NKT cells in cancer patients may be a result of a lack of stimulation. Furthermore, these data suggest, without wishing to be bound by theory, that autologous DC from cancer patients may not give the optimum level of stimulation that could be readily provided when utilizing the aAPC system. In addition, without wishing to be bound by theory, these data may help to explain the lack of a significant in vivo response following direct α-GalCer injections or adoptive transfer of autologous α-GalCer pulsed DC that researchers have found in clinical trials.

Without wishing to be bound by theory, it is believed that ex vivo expanded NKT cells may play a role in facilitating the anti-tumor activity of antigen specific CTL. To examine the potential of aAPC-stimulated cells, freshly isolated CD8$^+$T cells from PBMC were stimulated with aAPC for 7 weeks. Starting from 1×10$^6$ total CD8$^+$ T cells, cultures expanded to approximately 10$^9$ CTL after 7 weeks of culture. aAPC expanded CTL were 85% antigen-specific by the third week, remaining at this level throughout the rest of the expansion period. Since the starting population was less than 0.05% Mart-1-specific this represents minimally a 10$^6$-fold expansion of antigen-specific cells in less than two months. Another important criterion in evaluating CTL efficacy is recognition of endogenous target antigen-HLA complexes. Therefore, the ability of aAPC-induced CTL to recognize endogenous Mart-1 antigen in melanoma cells was studied (data not shown). Mart-1-specific aAPC induced about 68% IFN-γ-specific CTL, as determined by ICS staining after stimulation with Mart-1 pulsed T2 cells (data not shown). Importantly, these cultures were able to recognize melanoma cells that were HLA-A2 positive, 37.5% produced IFN-γ when stimulated with HLA-A2$^+$/Mart-1$^+$ allogeneic melanoma cells. In contrast, when stimulated with HLA-A2$^-$/Mart-1$^+$ allogeneic melanoma cells no cytokine production over background was detected (data not shown). In addition the same CTL recognized and killed allogeneic melanoma cells in an antigen specific fashion in a standard $^{51}$Cr release assay (data not shown). Thus, aAPC-induced CTL were able to recognize endogenous antigen-HLA complexes.

Figure 7:
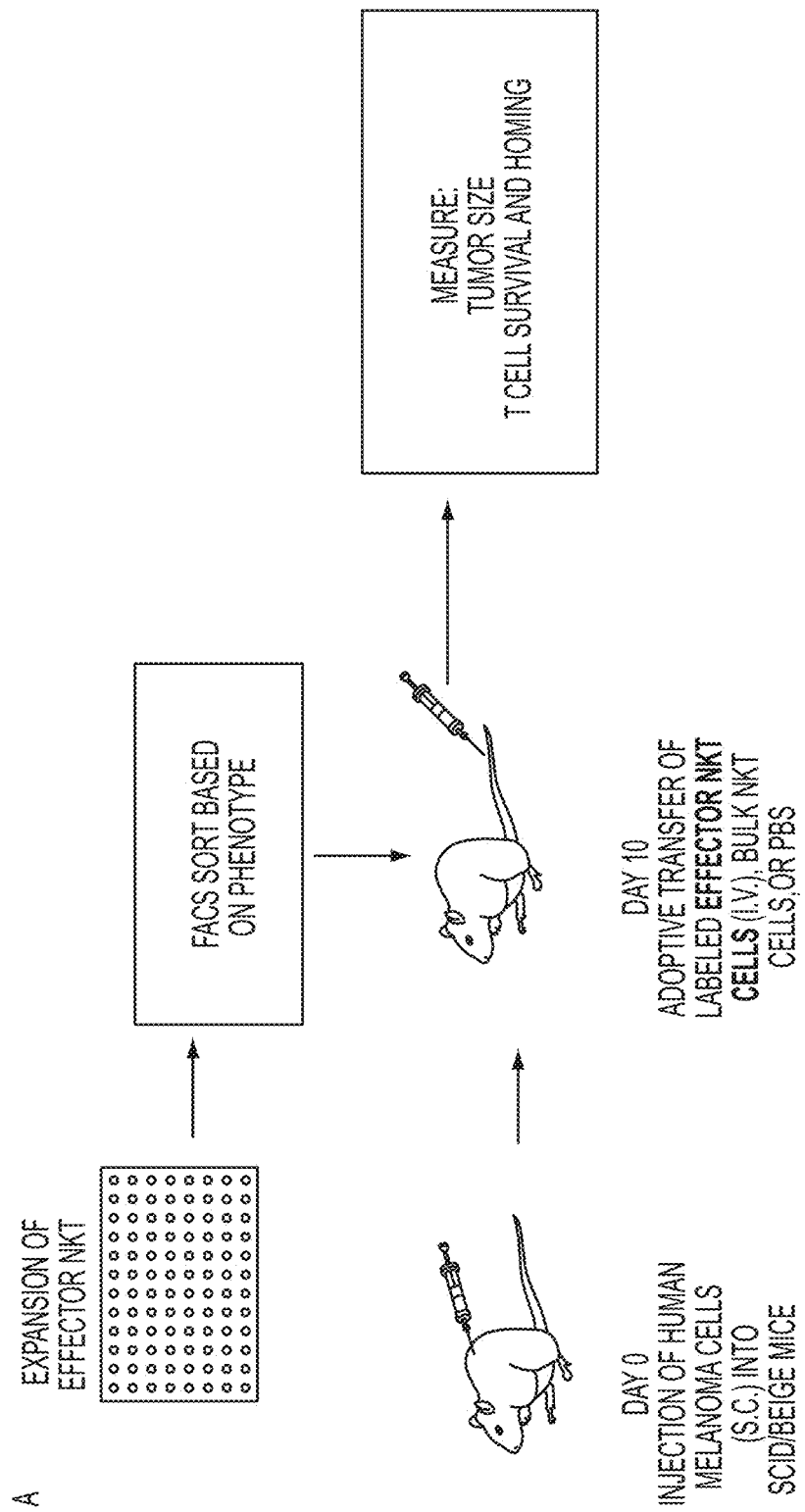
FIG. 7 shows murine study designs. Panel A shows in vivo efficacy of ex vivo expanded NKT cells. To evaluate the effect of aAPC expanded NKT cells one can inject BML melanoma cells (s.c.) and once the tumor reaches 5 mm one can inject effector NKT cells. Then monitor tumor growth and track activated NKT cells to the tumor site can be undertaken. Panel B shows analysis of the in vivo helper function of NKT cells. To evaluate if effector NKT cells can enhance the anti-tumor effects mediated by MART-1 specific CTL one can co-transfer labeled NKT cells and CTL. Then one can compare tumor size in mice in the presence and absence of CTL.
Figure 7:
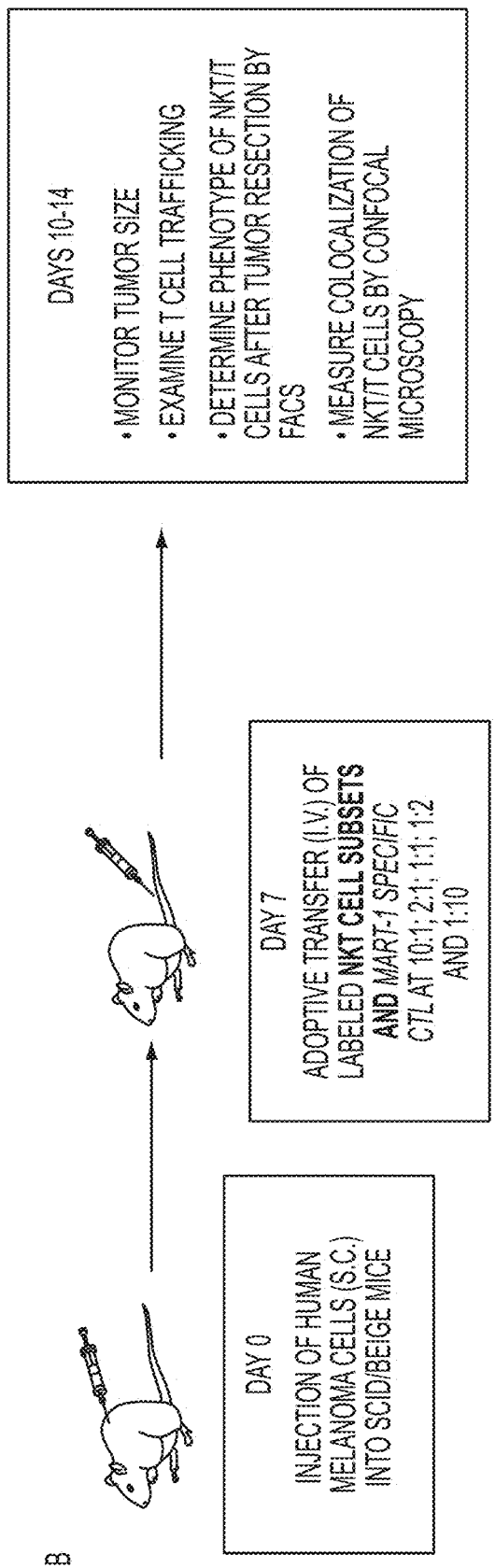

Next, the in vivo efficacy of Mart-1-specific CTL in an experimental human/SCID model was tested. In vivo human/SCID models, are often used to study adoptively transferred CTL. While the human/SCID models are by their nature only partially reconstituted immune responses, several of these models have been shown to have efficacy in studying adoptive immunotherapeutic treatments approaches for cancer. The inventors recently developed a similar human/SCID model to study the in vivo efficacy of aAPC induced Mart-1 specific CTL to eliminate melanoma tumor cells. Preliminary data indicates that aAPC induced Mart-1 specific CTL successfully inhibited the development of human melanoma tumors in SCID/Beige mice. Studies have shown that an injection of 1.5×10$^6$-Mart-1 specific CTL significantly inhibit tumor growth in mice injected with 5×10$^6$ HLA-A2$^+$/Mart-1$^+$ (Mel493) melanoma cells but not in mice injected with HLA-A2$^-$ control tumor. Thus aAPC induced CTL specifically inhibit HLA-A2/MART-1$^+$ tumor growth in vivo. Collectively, without wishing to be bound by theory, the studies using human CTL in a SCID mouse model showed that HLA-Ig based aAPC represent a robust approach for T cell stimulation and expansion in vitro. These studies have clear translational applications. While there was a significant decrease in tumor growth following adoptive transfer of MART-1 specific CTL, the CTL did not completely clear the tumor. The addition of effector NKT cells can increase the efficacy of the MART-1 specific CTL in this system. Murine studies that may be conducted are shown in FIG. 7, panels A and B.

Further studies may involve In vitro characterization of effector NKT cell subpopulations in healthy volunteers. First, the impact of varying CD1d-TCR affinity and costimulation on the development and expansion of NKT cells subsets will be evaluated. Recently, it has been reported that soluble forms of recombinant CD1d molecules loaded with antigen are able to directly target NKT cells in vitro. Since the engagement of the T cell receptor (TCR) by the CD1d/antigen complex is a fundamental requirement of T cell activation, our immobilized CD1d/antigen complexes offer a novel method to isolate, activate, and expand NKT cells for therapeutic use. Therefore the induction/expansion of effector NKT cell subpopulations by iGb3 or α-GalCel loaded aAPC may be analyzed. Both α-GalCer and iGb3 are important ligands for the study of CD1d-mediated activation of NKT cells, nevertheless it is not clear how to best activate NKT cells to ensure effective anti-tumor responses, rather than the induction of anergy. Therefore in these studies one can vary the following parameters: 1) the TCR affinity; 2) the ratio of signal 1 to signal 2; and 3) the type of signal 2 delivered to study requirement for optimal NKT cell activation. The TCR affinity can be varied using two different lipid antigens, α-GalCer and iGb3. The type of costimulation can be analyzed by generating aAPC with various costimulatory complexes, such as anti-CD28, CD44, CD40, and CD161. In the presence of a strong signal 1, such as seen when NKT cells are initially stimulated with α-GalCer, costimulation may not be needed. However in the presence of weaker affinity ligands such as iGb3 a costimulation complex may be used. In addition, without wishing to be bound by theory, it is believed that not all forms of costimulation are equivalent and that optimal stimulation by ligands with weak affinity requires more than one type of costimulation.

Given that Vα24$^+$NKT cells only constitute 0.01-2% of the T cell population in peripheral blood, the NKT cell population can be enriched from PBMC by using magnetic cell sorting for the CD3$^+$ or Vα24$^+$ population. In these experiments one can vary type of antigen on the aAPC and measure proliferation and cell death. To explore the growth potential of aAPC-stimulated NKT cells, every seven days one can harvest and count the cells. Cell viability can be determined by trypan blue exclusion. One distinct advantage of using aAPC is that instead of expanding the initial NKT cell population with whole PBMC, NKT cells can be preselected directly through binding to the conjugated lipid-antigen/CD1d-Ig complex and afterwards stimulated to proliferate. An important difference between cellular APC and aAPC may be the duration and strength of stimulation. For example, recognition of DCs by CD8$^+$T cells ultimately leads to lysis, thereby elimination of the antigenic stimulus. NKT cells may use a similar mechanism to terminate stimulation. However, NKT cells may not have an effective means of eliminating antigen presented by aAPC, thus stimulation by aAPC could potentially extend for hours or even days. On the other hand it has been described that NKT cells can be easily eliminated through activation induced cell death (AICD). Therefore, one can perform time course experiments to test the duration of stimulation. Cultures can be stimulated for variable amounts of time (about 0.5, 2, 6, 12, 36 hours as well our standard 7 day protocol). The aAPC can be separated from the NKT cells by vigorous pipetting to disrupt any conjugates. The aAPC can then be removed from the culture by using a strong magnet. One may initially study the effect of time utilizing our human NKT cell lines. Conditions can be established under which one can recover >95% of the aAPC beads with <5% cell loss. The cells can then be placed back in culture and their functional activity analyzed by cytokine production and their ability to lyse target cells.

Next, examination of the impact of varying co-stimulatory ligand complex on aAPC stimulation may be undertaken. T cell activation requires delivery of a combination of signals through the T cell receptor (Signal 1) and through co-stimulatory molecules (Signal 2) such as engagement of CD28 by B7. One of the parameters that one vary using aAPC is the ratio of signal 1 to signal 2 as well as the type of signal 2 delivered. In preliminary studies, a ratio of CD1d-Ig to anti-CD28 of 1 to 1 has been used. Here one may study the impact of varying ratios of CD1d-Ig to anti-CD28, to analyze the impact of using different co-stimulatory ligands (i.e. CD40, CD44, CD161) coupled to the beads, and to determine the optimal duration of stimulation. Illustrative ratios of CD1d-Ig to anti-CD28 are 30:1, 10:1, 3:1, 1:1, 0.3:1, 0.1:1, and 0.03:1. In these experiments, the total amount of protein used to couple to beads can be kept constant at 50 µg/4×$10^8$ beads. Studying aAPC-mediated cell expansion, acquisition of in vitro effector functions, and analysis of homing receptors can determine the efficacy of stimulation.

Further studies may evaluate APC efficacy in vitro. One can evaluate various formulations of aAPC using established assays as well as to incorporate additional assays to further help evaluate in vitro efficacy, which should be reflected in in vivo cytokine production and cytotoxic activity. The assays can include analysis of specific cell lysis, intracellular cytokine production, cytokine release, and expression of homing receptors to determine the efficacy of stimulation. Experiments can examine the phenotype of the expanded NKT cells subpopulation by flow cytometric analyses, for example by characterizing the phenotype by determining cell surface expression of Vα24, Vβ11, CD4, CD8, CD161, CD16, CD56, CD57, CD28, and CD44. Vβ chain usage can be assessed by semi-quantitative and real-time PCR. NKT cell subpopulations ($CD4^+$, $CD8^+$, or $CD4^-CD8^-$) can be separated by magnetic cell separation. The NKT cell subpopulations can be cultured with leukemia and lymphoma cell lines, U937, THP-1, and Jurkat, which have been shown to be lysed by NKT cells, and one can assess their function by cytokine release and cytotoxicity assays.

Although NKT cells play a major role in anti-tumor defense, some studies have shown a suppressive role for NKT cells in the control of tumors. Using the inventors' large numbers of CMV and MART-1 specific CTL, this system can be used to develop NKT cell suppressor assays. Standard cytotoxicity assays using antigen specific CTL and peptide pulsed T2 cells can be established and the ability of specific NKT cell subsets ($CD4^+$, $CD8^+$, and $CD4^-CD8^-$) to inhibit target cell lysis evaluated.

In addition to generating NKT cells with appropriate effector functions, another potentially important parameter for their efficacy is expression of homing receptors that allow them to traffic to sites of pathology, as has been characterized for antigen specific CTL. Currently effector CTL efficacy has been linked to the following phenotype of homing receptors, $CD62L^+$, $CD45RO^+$, and $CCR7^-$, which are expressed on specific NKT cell subsets (see Table 1). Since mAb recognizing all of these receptors are commercially available, aAPC induced/expanded NKT cell populations can be characterized for the expression of these homing receptors. Since this analysis could theoretically require 5 color analyses of NKT cell subsets, one can analyze homing receptor expression in the cultures that have been first separated based on their expression CD4 or CD8 and perform a 4 color analysis.

In these studies it is believed, without wishing to be bound by theory, that stimulation with α-GalCer loaded aAPC, compared to iGb3 loaded aAPC can result in a greater expansion of NKT cells within 2 weeks. One may find that after several weeks of stimulation the cells stimulated with iGb3 may have greater functional activity (cytokine production and cytolytic activity). It is expected to find most of the cytokine production and cytotoxic activity in the $CD4^+$ and $CD8^+$ subsets, compared to the DN ($CD4^-CD8^-$) population. Most likely a discrete subset of $CD4^+$ NKT cells can be suppressive. The molecules listed in Table 1 can be evaluated to characterize this subset.

Next, an investigation of the in vivo efficacy of aAPC generated NKT cells may be conducted. One may determine the role of effector NKT cells in anti-cancer immune responses using a mouse model system. For example, human/SCID models have been developed to study adoptively transferred human CTL. One model (Int J Cancer 81:486) has focused on using adoptively transferred CTL to eliminate a subcutaneous implanted human melanoma line, such as Mel493 ($HLA-A2^+$/$MART-1^+$). This model can be used to examine whether the transfer of ex vivo expanded effector NKT cells can delay the onset and/or growth of the tumor (see e.g. FIG. 7). Briefly, SCID mice can be conditioned by irradiation, then one day later animals can be injected s.c. with the melanoma tumor cell line, Mel493. aAPC-expanded NKT cells can be injected once the tumor reaches 5 mm in diameter. Control animals can receive injections of PBS or bulk NKT cells. Each experimental group may consist of ten animals with a total of three groups (optimized effector NKT cells, bulk NKT cells, and PBS) for each experiment. Tumor growth can be monitored. Readout is a comparison of tumor growth in the three groups. Differences in survival between different groups are assessed using the log-rank test. Procedures involving the comparison of data from groups of individual animals first has the equality of variance examined using the F test (two groups) or Levene's test (multiple groups). When variances are not equal, log transformations are performed. When normally distributed sample means are to be compared, the Student's t test (two groups) can be used. Statistical significance can be defined as $p<0.05$. Alternatively or in combination, one can study the homing of NKT cells to the side of an established tumor. Once the tumor reaches 5 mm in diameter one can inject Cell Tracker—CMFDA labeled NKT cells to show that adoptively transferred NKT cells track to the site of the tumor. One can analyze the tumor for infiltrating human NKT cells on days 1, 3, 5 post transfer using flow cytometry and confocal microscopy. The experiments described above can be useful in understanding the in vivo efficacy of aAPC-expanded NKT cells. NKT cells can also be rescued from the mice and analyzed for cytokine secretion and lytic activity.

Next one may examine the helper function of NKT cells in vivo by co-transfer of CTL and NKT populations. The addition NKT cells to tumor specific CTL can be important for a successful T cell immunotherapy. Mart-1 is a melanocyte differentiation antigen, therefore MART-1 specific $CD8^+$ T cells expanded from the HLA-A2 positive individuals used in above description can be co-transferred in order to examine the helper function of NKT cells. The Mart-1 peptide represents a low affinity response typical of many anti-tumor specific CTL responses. A melanoma peptide to be used may be the modified Mart-1 peptide (ELAGIGILTV)(SEQ ID NO:1), as described *Int Immunol* 11: 1971. This peptide has a higher affinity for HLA-A2, without influencing the binding of the Mart-1 peptide/HLA-A2 complex to the TCR. Studies by the inventors have shown that aAPC made by coupling A2-Ig and anti-CD28 mAb to particles can be used to induce and expand antigen-specific CTL. There is evidence that Mart-1-loaded aAPC-stimulated PBMC cultures resulted in up to 84.3% Mart-1 specific CTL as determined by intracellular cytokine staining (data not shown). Therefore, to analyze and evaluate the function and importance of helper NKT cells in the setting of an adoptive CTL transfer in vivo, one can repeat the adoptive T cell transfer experiments described above using a mixture of tumor specific CTL and effector NKT cells at the following ratios 10:1; 2:1; 1:1; 1:2 and 1:10 with a constant number of NKT cells, defined by earlier experiments. The results can be compared to those previously obtained. A synergistic of highly additive effect is predicted, without wishing to be bound by theory. The addition of NKT cells may help the CTL to fully eliminate the tumor. NKT cells alone may be able to completely clear the tumor.

Further, one may compare effector NKT cells subpopulations in healthy controls and cancer patients. For instance, a comparison of proliferation in NKT cell populations isolated from cancer patients to the expansion rates of NKT cells isolated from normal controls may be undertaken. Cancer patients have been shown to have defects in both NKT cell and DC function. It is therefore critical to study the stimulation of effector NKT cell subsets by aAPC, from patients with disease. In these studies, the NKT cell population can be enriched by using magnetic cell sorting for the $CD3^+$ or $V\alpha24^+$ population. Next, one can analyze the induction/expansion of NKT cell subpopulations by iGb3 or $\alpha$-GalCel loaded aAPC. Specifically, NKT cells can be cultured with CD1d-Ig (+/− costimulatory molecules) -expressing aAPC. These experiments can be modeled by previous experiments outlined above. To explore the growth potential of aAPC-stimulated NKT cells in cancer patients every 7 days cell viability and proliferation can be measured. Also, at this time the old aAPC can be removed and the cells can be washed and restimulated.

One may also characterize the phenotype and function of aAPC expanded NKT cell subsets isolated from cancer patients. Experiments can examine the phenotype of the expanded NKT cells subpopulation by flow cytometric analyses. The different NKT cell populations ($CD4^+$, $CD8^+$, or DN) can be separated by FACS cell sorting. To analyze their functionality in vitro one can culture them with leukemia and lymphoma cell lines (U937, THP-1, Jurkat) and measure cytokine release and cytolytic activity.

Also, to test the in vivo efficacy of NKT cells from cancer patients one can examine the ability of aAPC-generated NKT cells from cancer patients to eliminate tumors in a human melanoma/SCID model system. These experiments can use aAPC expanded effector NKT cells that have the best potential derived from the in vitro studies described above. To evaluate the efficacy of these cells one can monitor tumor growth and track activated NKT cells to the tumor site. In addition, one can use MART-1 specific $CD8^+$ T cells expanded from the same individuals in order to examine the helper function of NKT cells. In these studies one can also monitor survival, weight, and tumor growth and metastasis.

Adoptive Transfer Mediated Generation of NKT Cells and Antigen Specific CTLs from Adult Stem Progenitor Cells Here the adoptive transfer a relatively low number of NKT cells is proposed with the expectation that one can enhance anti-tumor responses and mediate protection against infections in transplant recipients. Here a focus is on CD1d-mediated NKT cell activation. Data demonstrates that NKT cells are significantly reduced in lymphomas patients, which limits the host's tumor immunosurveillance and impedes anti-tumor immune responses. Restoration of this specific population of T cells can significantly impact lymphomagenesis. Thus one may generate NKT cells and antigen specific CTLs from adult stem progenitor cells using the OP9-DL1 system in combination with artificial antigen presenting cells. These studies have the potential to significantly transform the field because while we anticipate that modulating NKT cells alone can enhance innate and adaptive immune responses to lymphoma, our therapeutic strategy can be used in combination with current targeted approaches such as ibrutinib, which inhibits Bruton's tyrosine kinase, as well as other forms of immunotherapy such as antigen specific lymphocytes.

NKT cells are reduced in Cancer Patients. As a precursor to generating NKT cells from HSPC, the percentages of NKT cells and classical T cell subsets in a panel of healthy donors and lymphoma patients was first examined. The percentage of circulating NKT cells was significantly lower in cancer patients, independent of tumor type. Percent NKT cells were assessed in healthy donors and newly diagnosed lymphoma patients prior to treatment or surgery. The percentage of NKT cells was $0.08\pm0.01$ in cancer patients (N=55) compared to $0.22\pm0.05$ in healthy donors from all studies (N=39). Analysis of the frequency of classical T cell subsets in the total PBMCs showed a high degree of variability, but no consistent differences were noted. Next NKT cells in the bone marrow and peripheral blood of lymphoma patients was evaluated. It has been reported that tumors can shed factors that inhibit NKT cell activation into the tumor microenvironment. In each of ten non-Hodgkin lymphoma (NHL) patients, the percentage of NKT cells was lower in the peripheral blood than in the bone marrow (data not shown). These data substantiate the idea, without wishing to be bound by theory, that circulating NKT cells are reduced in patients with systemic malignancies. Furthermore, while the levels of NKT cells are higher in the bone marrow than in the peripheral blood, their absolute numbers remain inadequate for clinical application.

Generation of human T cells using OP9-DL1 cultures. Based on the low absolute numbers of NKT cells, a more clinically practical situation was obtained by developing cells by differentiating NKT cells from adult progenitor stem cells. Human $CD34^+$ HPC were seeded on the OP9-DL1 feeder layer and proliferation and differentiation were studied using CD34, CD38, $V\alpha24$, $V\beta11$, CD4, CD8, CD3, and $TCR\gamma\delta$ as postselection markers. Phenotypically mature T cells could be easily discerned in the cultures because as time progressed the cells lost expression of CD34 and CD38, transitioned to double-positive lymphocytes, and then primarily to $CD4^+CD3^+$ T cells. CD34 expression decreased as the cells became $CD3^+$ in the presence of Notch signaling (expression of DL1) in OP9 stromal cells (data not shown).

Expansion of Primary NKT cells using (aAPC). Expanded T cell subsets were largely $V\alpha24^-$ and bead based-CD1d-expressing artificial antigen presenting cells (aAPC) have been used to expand human NKT cells in vitro. Thus, OP9-DL1-generated primary T cells were co-cultured with $\alpha$-GalCer-loaded aAPC. The expanded population was mostly $CD8^-$NKT cells. It was found that these cells produced IFN-$\gamma$ as well as GM-CSF and IL-4 (data not shown) following stimulation. Given the above phenotypic and functional characteristics, without wishing to be bound by theory, it is posited that adult human bone marrow stem progenitors cells can be used to generate functionally mature NKT cells. In fact, data was obtained from a patient with Hodgkin's lymphoma. Specifically, $3\times10^5$ $CD34^+$ cells were isolated from the bone marrow and cultured for 3 weeks. Then $2\times10^6$ T cells were cultured with $\alpha$-GalCer loaded aAPC and obtained $4\times10^6$ NKT cells were obtained. Importantly, it has been demonstrated that this method can be used to generate NKT cells from the bone marrow HSPC of healthy donors as well as lymphoma patients. A goal of the of prophetic studies described herein is to use this novel system to generate NKT cells from progenitor cells obtained from G-CSF mobilized blood of, for example, lymphoma and myeloma patients.

Figure 8:
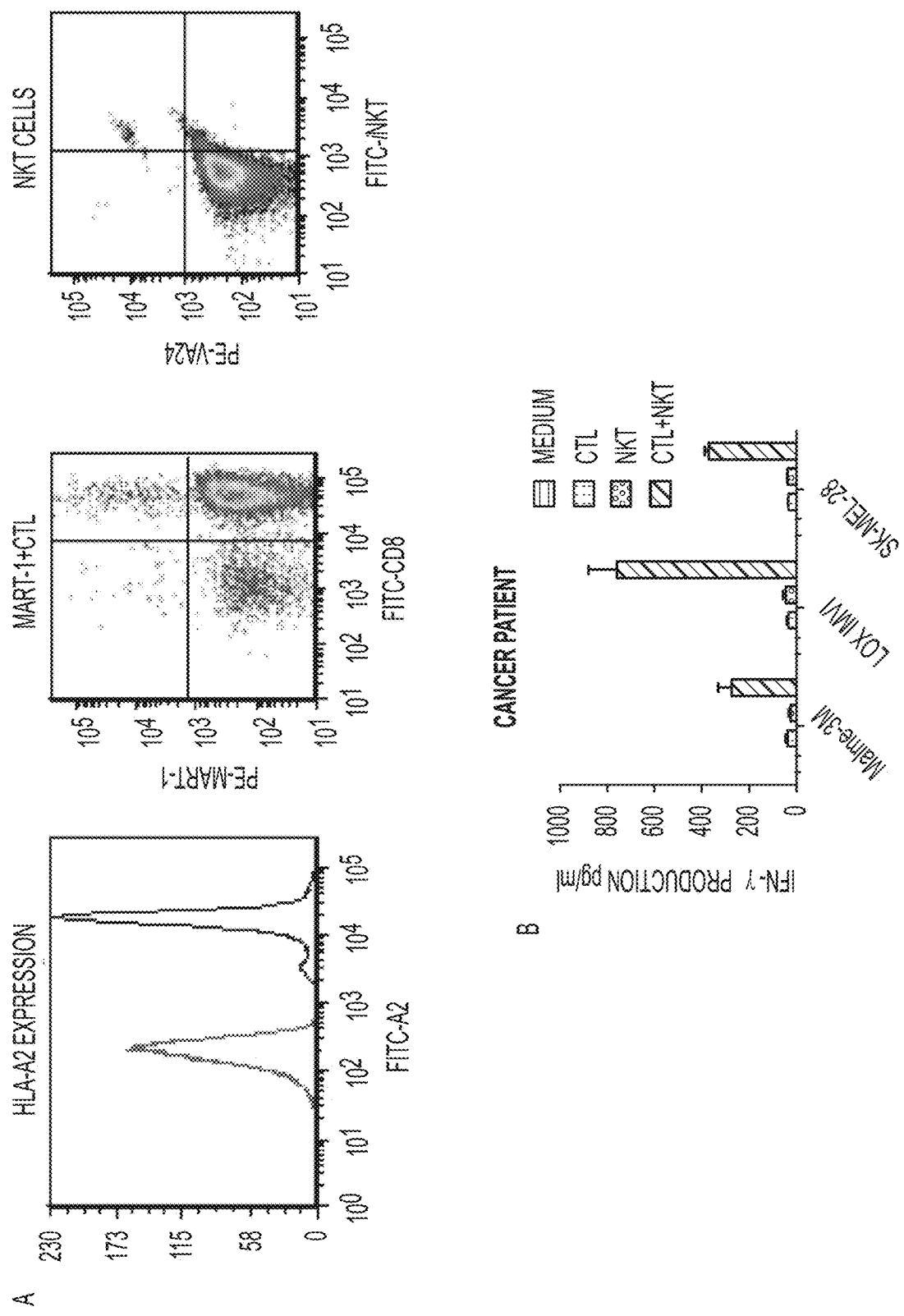
FIG. 8 shows aAPC-expanded CTL/NKT cell responses to melanoma. Panel A shows lymphocytes from HLA-A2+ donors were expanded by aAPC. NKT cells and $MART-1^+$ CTLs were assessed by flow cytometry. Panel B shows following expansion, melanoma patient NKT cells and MART-1 specific CTL were cocultured melanoma cell lines in the presence of MART-1 peptide and CD1d expressing feeder cells. Medium served as a negative control.

NKT cells enhance antigen-specific CTL responses. Both melanoma specific (MART-1$^+$) CTL and NKT cells from peripheral blood lymphocytes have been expanded (FIG. 8). First, the initial PBMC population for HLA-A2 expression was examined, and if positive both MART-1$^+$CD8$^+$ T cells and NKT cells are expanded using aAPC (FIG. 8, panel A). As shown in FIG. 8, panel B, co-culture of NKT cells and CTLs from the same donor result in enhanced IFN-γ production. This synergistic response is not HLA-A2$^+$ specific. Both HLA-A2$^+$ and HLA-A2$^-$ cell lines have been transfected with CD1d molecules. CD1d-expression on the tumor cells does not dictate the response (data not shown), specifically NKT cells cultured in the presence of antigen-specific CTL results in high IFN-γ production, independent of HLA & CD1d expression. These data are provocative and the proposed studies can determine if this response is tumor-dependent/specific and if IFN-γ responses correlate with cytotoxicity.

An OP9-DL1 system, in combination with aAPC, may be used to generate NKT cells from the stem progenitor cells derived from the peripheral blood of lymphoma and myeloma patients. Progenitor cells (CD34$^+$) can be isolated from banked G-SCF mobilized peripheral blood samples, not bone marrow, and cultured with OP9-DL1 stromal cells in order to generate T cells. Then NKT cells can be expanded from the T cell subpopulations using the present artificial antigen presenting cell system. The anti-tumor function of NKT cells expanded using different aAPC formations can be compared to develop the best co-culture conditions. Rates of cell expansion and cell death, as well as the phenotype of the expanded subpopulations can be monitored. The in vitro function of the expanded NKT cell subsets by cytokine production (cytokine ELISA & intracellular staining (ICS) and cytotoxicity assays ($^{51}$Cr-release, ICS, & DELFIA cytotoxicity assays purchased from Perkin Elmer).

Further one may determine the mechanisms by which aAPC-expanded NKT cells derived HSPC enhance antigen specific CD8 CTL cell responses by, for instance, utilizing the aAPC system to expand both NKT cells and antigen-specific CD8 T cells.

Further one may determine the in vivo efficacy of HSPC-derived NKT cells and antigen specific CTLs. In these studies, one can utilize a human melanoma/SCID-beige mouse model in which one can adoptively transfer the NKT cells generated and the MART-1 specific CTLs generated above. This set of experiments can be useful in understanding the in vivo efficacy of HSPC/aAPC-generated NKT cells. In addition, one can assess whether NKT cells work synergistically with CTLs in vivo. One model has focused on using adoptively transferred CTL to eliminate a subcutaneous implanted human melanoma line, such as Mel493 (HLA-A2+/MART-1+). This model can be used to examine whether the transfer of ex vivo expanded effector NKT cells can delay the onset and/or growth of the tumor. Briefly, SCID mice can be conditioned by irradiation, then one day later animals can be injected s.c. with the melanoma line, Malme-3M. HSPC/aAPC-derived NKT & CTLs can be injected once the tumor reaches 5 mm in diameter. Control animals can receive injections of PBS, NKT cells alone, CTL alone or both NKT and CTL. Each experimental group can consist of ten animals with a total of four groups for each experiment. Tumor growth can be monitored. Readout can be a comparison of tumor growth in the four groups. Statistical Analysis: Differences in survival between different groups can be assessed using the log-rank test. Procedures involving the comparison of data from groups of individual animals can have the equality of variance examined using the F test (two groups) or Levene's test (multiple groups). When variances are not equal, log transformations can be performed. When normally distributed sample means are to be compared, the Student's t test (two groups) can be used. Statistical significance can be defined as $p<0.05$. In a second approach, one can confirm that these HSPC derived NKT cells can specifically lyse B cell lymphomas in vivo by using a xenograft model, in which one can implant C1R-CD1d (a human B lymphoma line transfected with CD1d) into SCID-beige mice.

Stimulating NKT Cells with aAPCs

In some studies, the functionality of costimulatory molecules can be assessed using aAPC. While the intracellular signaling for conventional T cells is well understood, this information for NKT cells is as yet unavailable. Using aAPC to stimulate NKT cells, a thorough investigation of the intracellular signaling cascades using various different NKT cell ligands can be performed. These factors can yield other targets to boost NKT cells responses along with administration of activating ligands. CD1d-based aAPC can also be re-designed to include various costimulatory molecules. Since aAPC can be designed to express any costimulatory molecule, they can lead to immediate identification of potential activating signals that can be included during patient anti-tumor therapy. The use of aAPC for the activation of NKT cells facilitates the study of cellular proteins and signaling molecules. It also allows researchers to mimic various conditions of NKT cell activation since the precise mechanisms that drive different types of responses are not completely understood.

Figure 9:
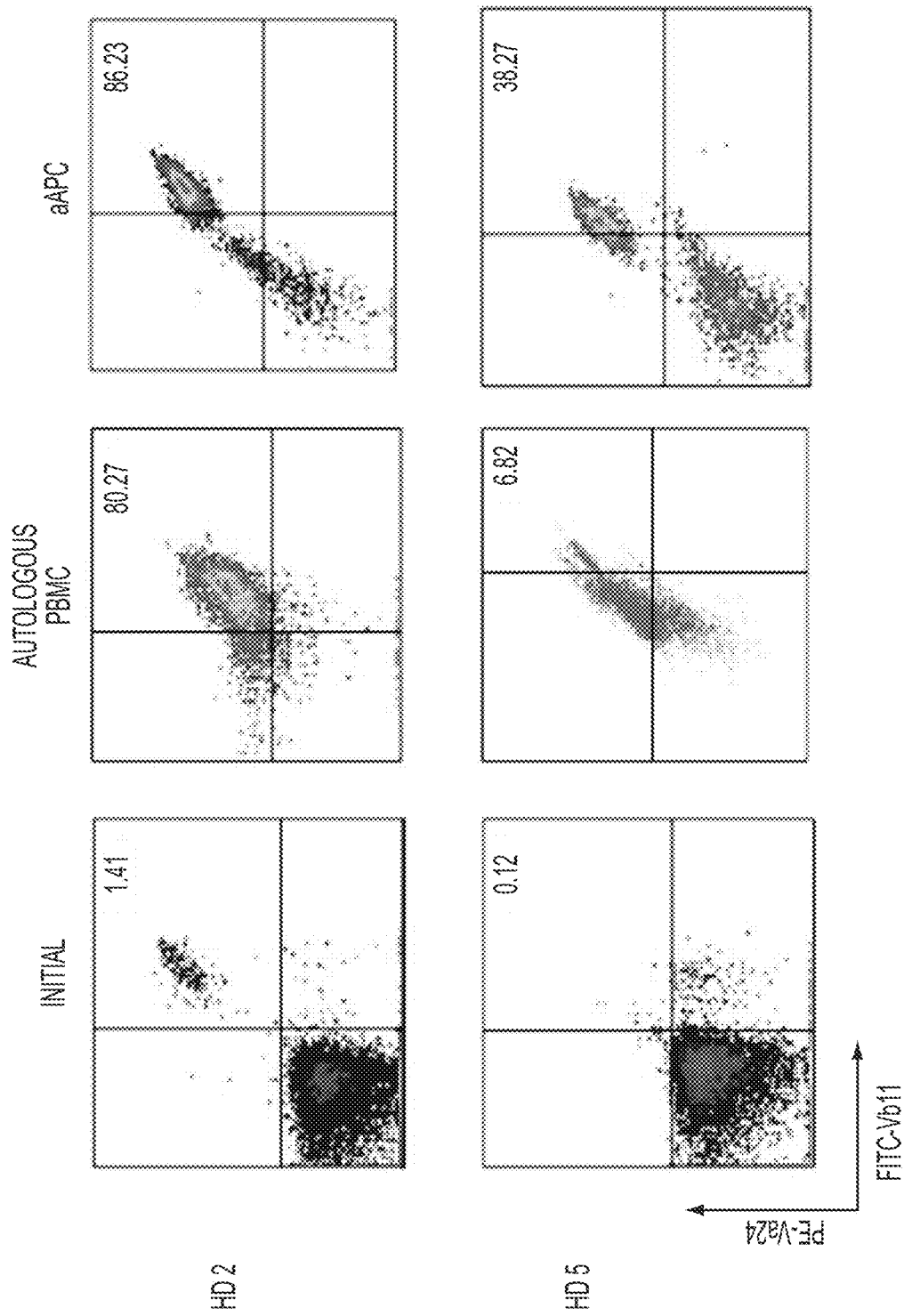
FIG. 9 shows CD1d-based aAPC can be used to expand human NKT cells. $CD161^+$ T cells were isolated from PBMC using magnetic bead separation. The cells were stimulated biweekly with irradiated PBMC pulsed with 100 ng/ml α-GalCer (10:1 ratio) or α-GalCer loaded aAPC±αCD28 (1:1 ratio). Data shown are after 2 rounds of stimulation.
Figure 10:
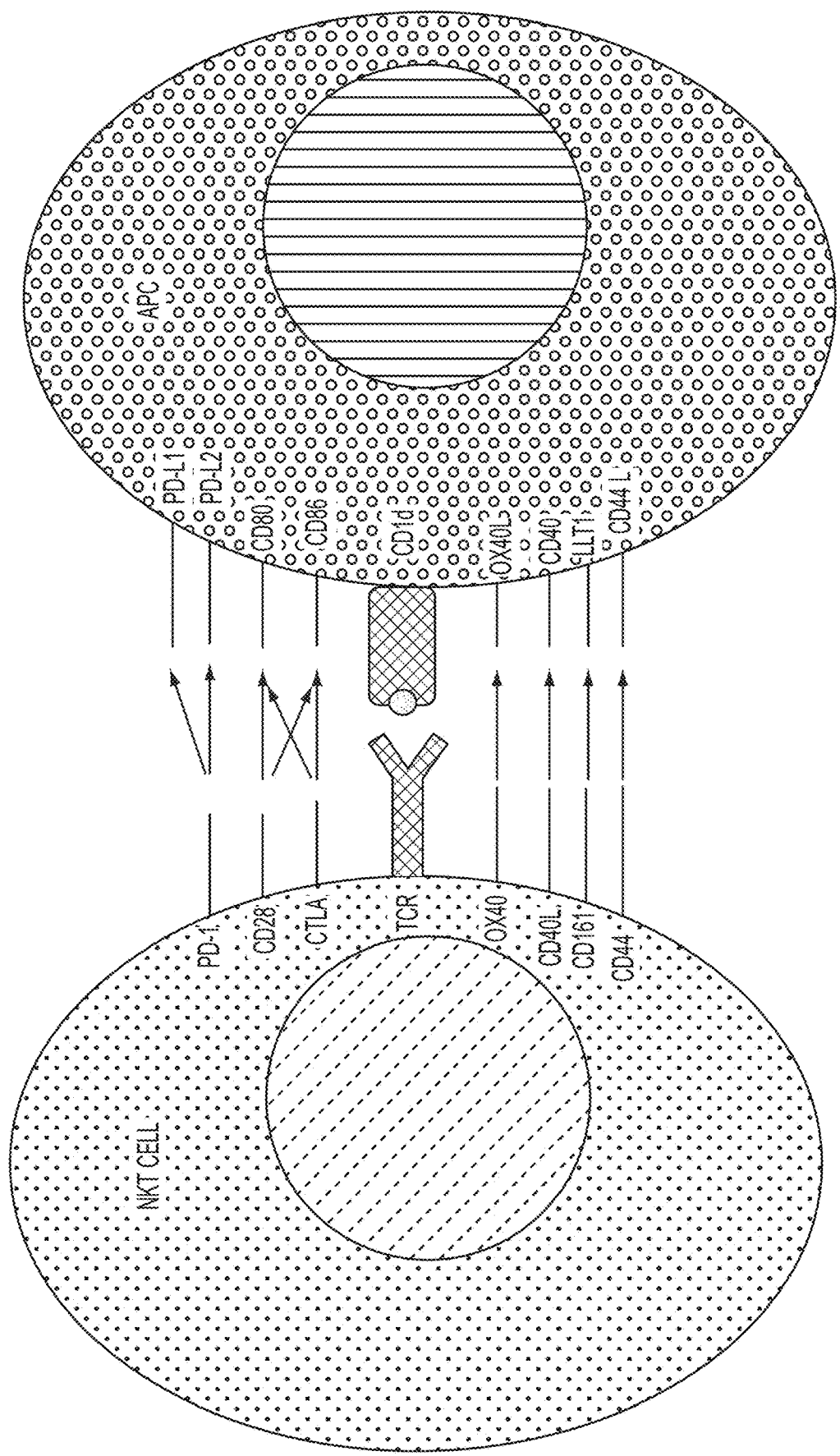
FIG. 10 shows potential costimulatory ligand-receptor interactions between NKT cells and antigen presenting cells. A selection of the key costimulatory molecule pairs involved in NKT cell activation is depicted. The CD1d- and TCR synapse is shown in blue and the lipid antigen is shown in red, CD28 co-stimulatory families are shown above the CD1/TCR and CD40 families are shown below. The arrow indicates cross-reaction between the receptor-ligand pair.
Figure 11:
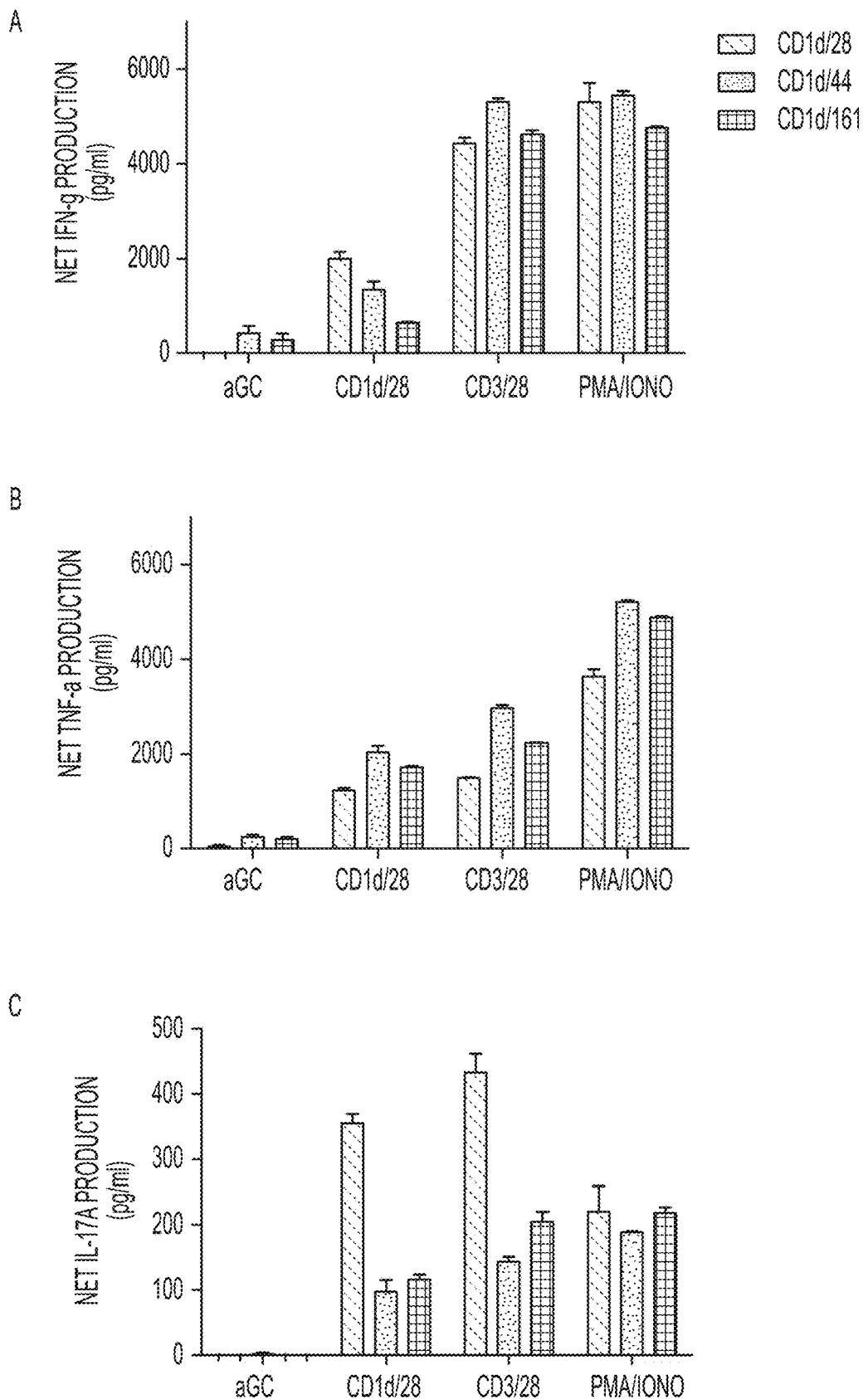
FIG. 11 shows cytokine profiles of aAPC-expanded NKT cells. After stimulation with α-GalCer loaded aAPC for two weeks, the expanded NKT cells ($1 \times 10^5$/well) were cocultured with soluble α-GalCer, PMA/ionomycin, αCD3/28 microbeads, or α-GalCer loaded aAPC ($2 \times 10^5$/well) for 48 hr. Panel A: IFN-γ, Panel B: TNF-α, and Panel C: IL-17 production was measured by standard cytokine ELISA. Data shown are net cytokine production after subtracting the negative controls (media and empty beads).

Initial studies have been conducted to examine the impact of varying co-stimulatory ligand complex on aAPC stimulation mediated expansion of NKT cells. T cell activation requires delivery of a combination of signals through the T cell receptor (signal 1) and through co-stimulatory molecules (signal 2) such as engagement of CD28 by B7. One of the parameters that one can vary using aAPC is the ratio of signal 1 to signal 2 as well as the type of signal 2 delivered. As depicted in FIG. 9, NKT cells express the majority of co-stimulatory molecules found on classic CD4$^+$ and CD8$^+$ T lymphocytes.

NKT-specific aAPC as adjuvants. Considering the unique adjuvant effect that occurs following NKT cell activation and its modulation other immune effectors, developing combination therapeutic regimens that activate NKT cells as well as promote adaptive immunity may be very useful.

Cytokine-mediated modulation of NKT cell function. NKT cells are known to rapidly produce large amounts of cytokines after activation. NKT cells are inherently capable of producing Th1 as well as Th2 cytokines. Administering cytokines along with aAPC can thus be a useful method to achieve robust NKT cell responses by engaging both—the antigen-dependent and the antigen-independent routes of NKT cell activation. aAPC can allow fine tuning of the immune response through administration of cytokines such as IFN-γ to directly boost the Th1 response, or indirectly using IL-12 to activate NK cells as well as NKT cells.

Polarizing NKT cell responses based on antigen. The types of responses seen by effector cells can be greatly altered depending on the type of antigen encountered by the effector cell as well as the antigen-presenting molecule. In the case of NKT cells different analogues of α-GalCer (PBS57, OCH, C-GalCer can elicit Th1 or Th2 responses. In addition to effector functions these lipid antigens can be used to initiate proliferation of NKT cells. Typically, autologous dendritic cells are pulsed with different lipid antigens and then incubated with NKT cells to determine which types of cytokines are secreted. This process is laborious and time consuming. aAPC can be incubated with desired antigen and provide a constant source of stimulation for the expansion and activation of NKT A number of different methods of delivery of α-GalCer have been demonstrated to effectively stimulate NKT cells, seen most often in the context of using these cells as vaccine adjuvants. α-GalCer is considered viable vaccine adjuvant because of its ability to stimulate NKT-mediated cytokine release and its related biological functions. The present aAPCS may be used in delivery of α-GalCer.

CD1-based aAPC may be used in, for example, the treatment of autoimmune diseases and allograft rejection.

Stimulating NKT Cells with aAPCs

Figure 13:
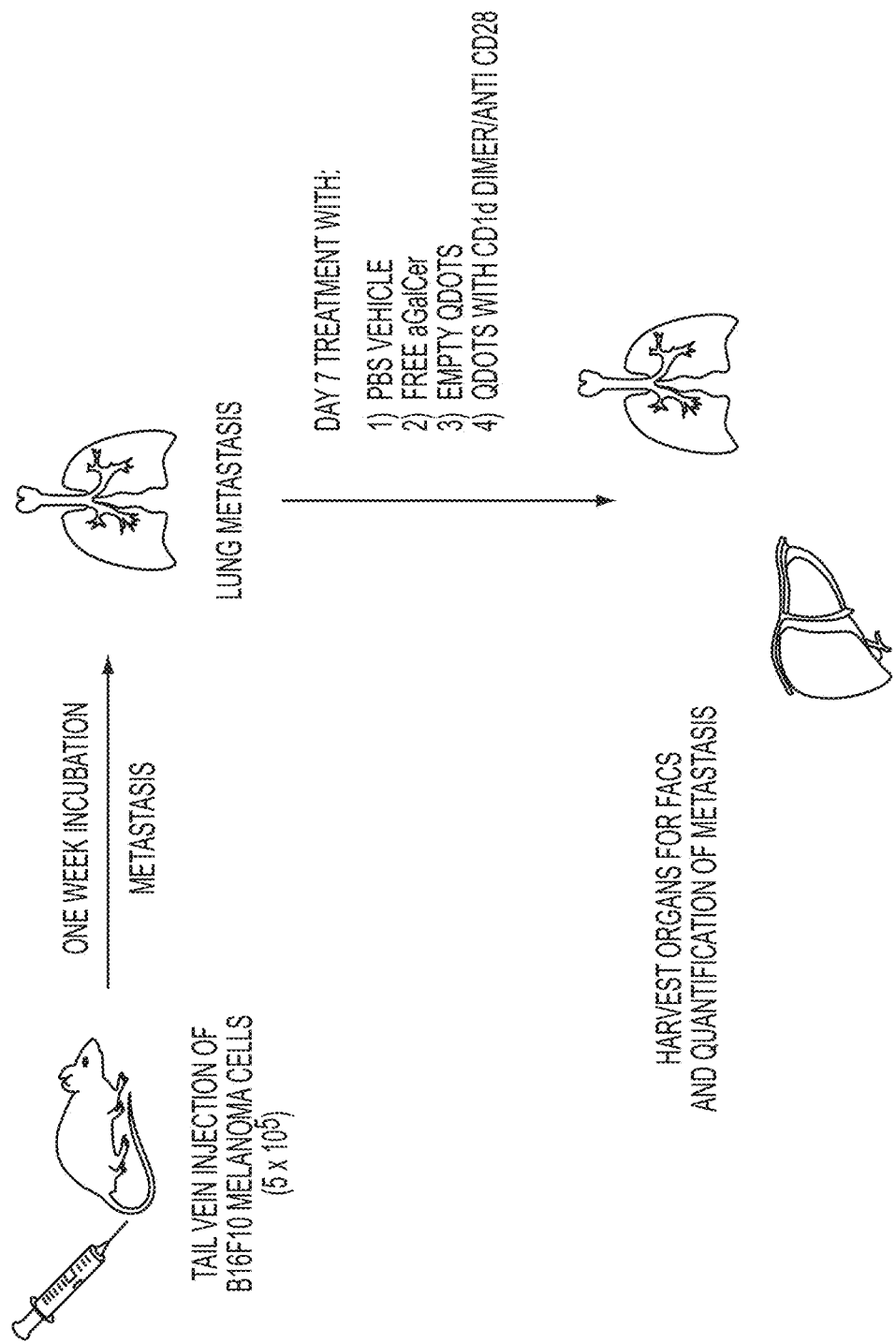
FIG. 13 shows a schematic of experimental design using nanoparticle based aAPC to activate NKT cells in vivo in a B16 melanoma lung metastasis mouse model.
Figure 14:
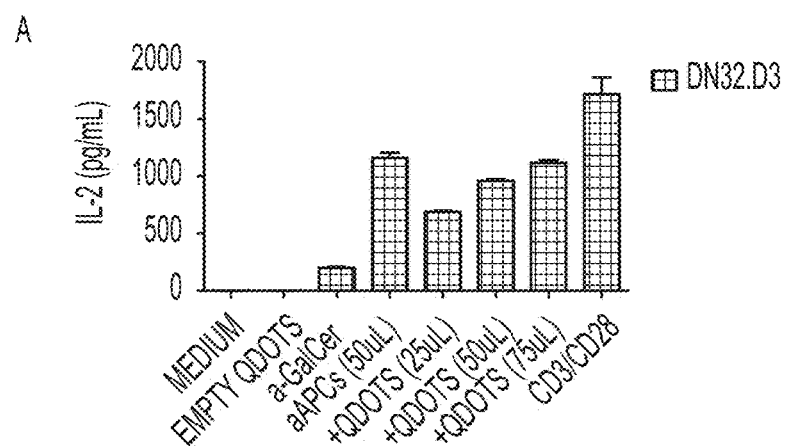
FIG. 14 shows nanoparticles can be functionalized and used to modulate immune responses in vitro and in vivo. Panel A shows CD1d-Ig and anti-CD28 mAb were conjugated to (Mots and loaded with antigen (α-GalCer) to generate Qdot-aAPC and compared to our standard bead aAPC. Panel B shows B6 mice were injected with B16-F10 melanoma cells i.v., on day 7 Qdots were injected i.v. and tumor clearance was assessed. Functionalized Qdots activated NKT cells in vivo and no toxicity was observed. Panel C shows B6 liver sections were stained with Qdot-aAPC. Qdots are fluorescent and are easily visualized.
Figure 14:
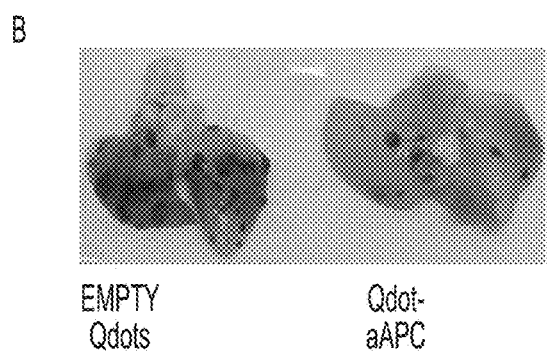
Figure 14:
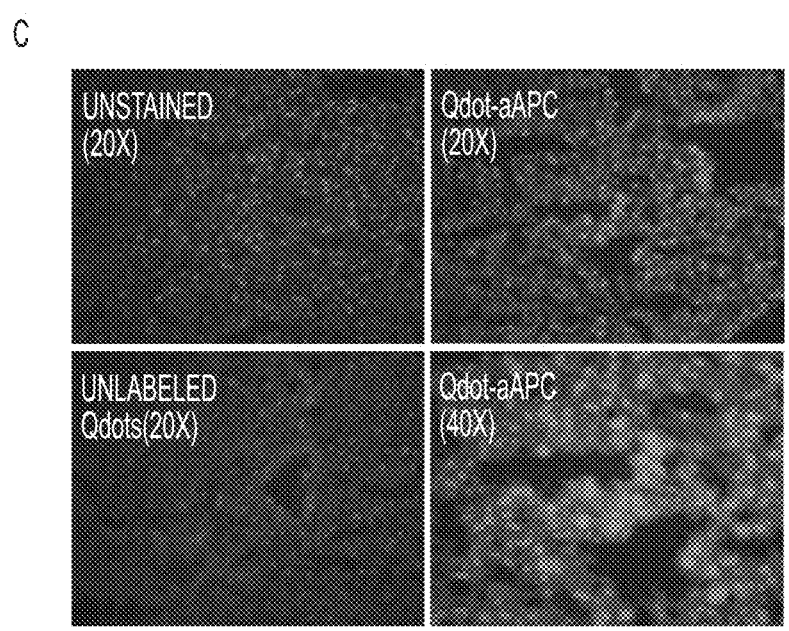

CD1d-Ig and anti-CD28 mAb were conjugated to Qdots and loaded with antigen (α-GalCer) to generate Qdot-aAPC and compared to standard bead aAPC (FIG. 14). Qdots are fluorescent and are easily visualized. These particles were effective in cancer treatment in mice (FIGS. 13 and 14).

Modulating NKTs Using aAPCs

Figure 15:
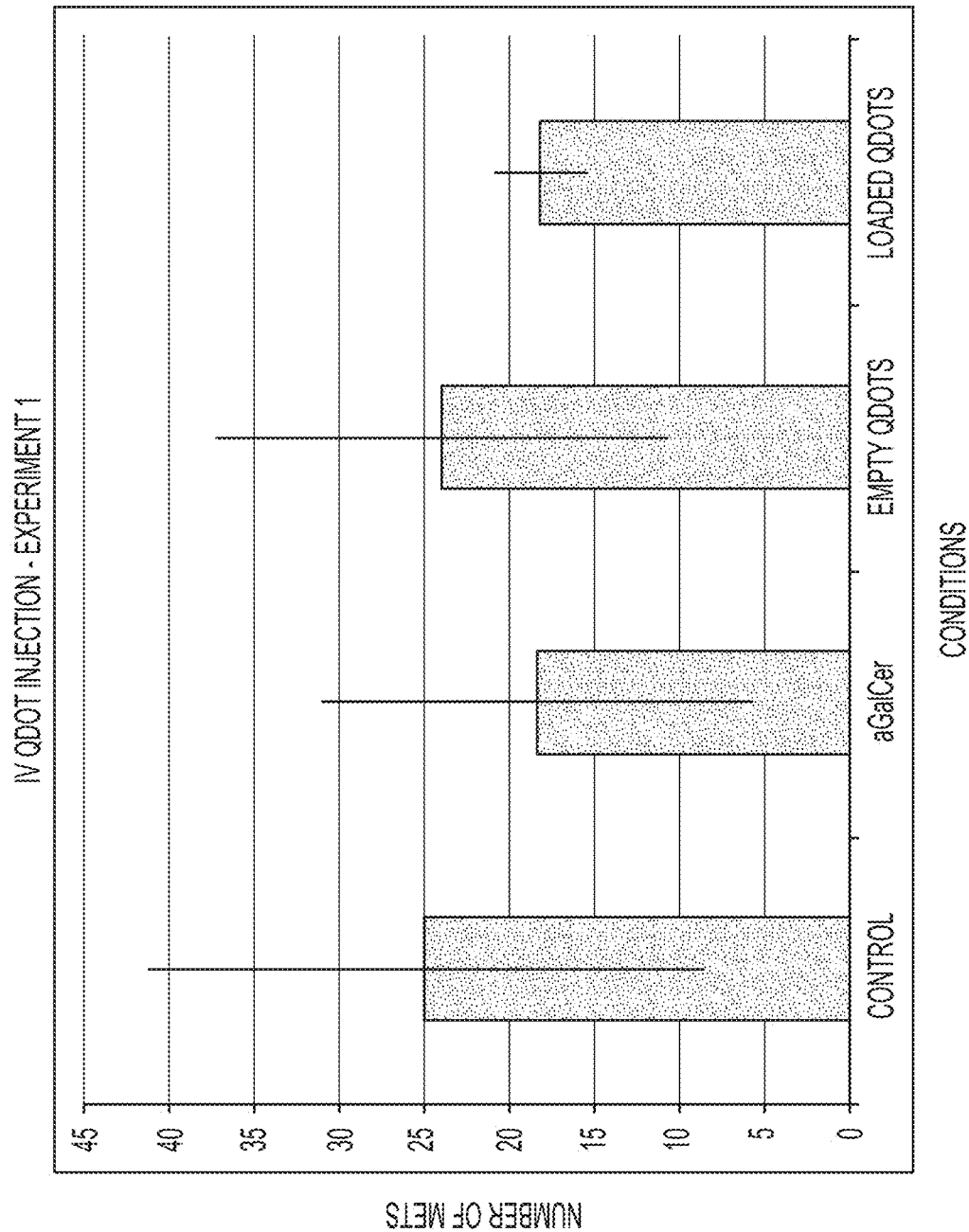
FIG. 15 shows B6 mice were injected with B16-F10 melanoma cells i.v., on day 7 Qdots were injected i.v. and tumor clearance was assessed. The total number of lung metastases was determined as shown here.
Figure 16:
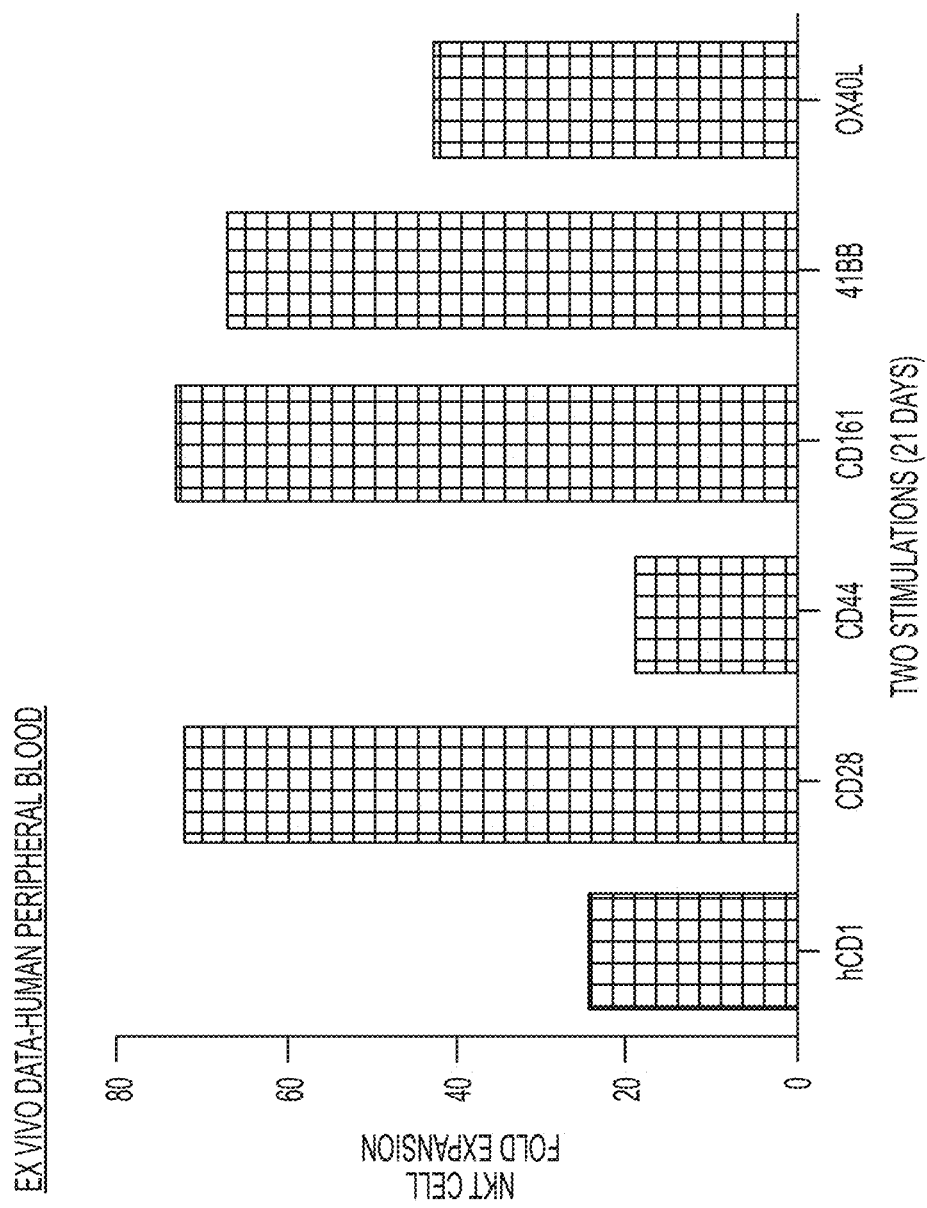
FIG. 16 shows the use of different co-stimulatory molecules (CD28, 44, 41 BB, OX40L) on aAPC differentially effect NKT cell expansion. The fold expansion is calculated by determining the percentage of NKT cells by flow cytometry and multiplying % NKT cells by the total number of cells in the culture.
Figure 17:
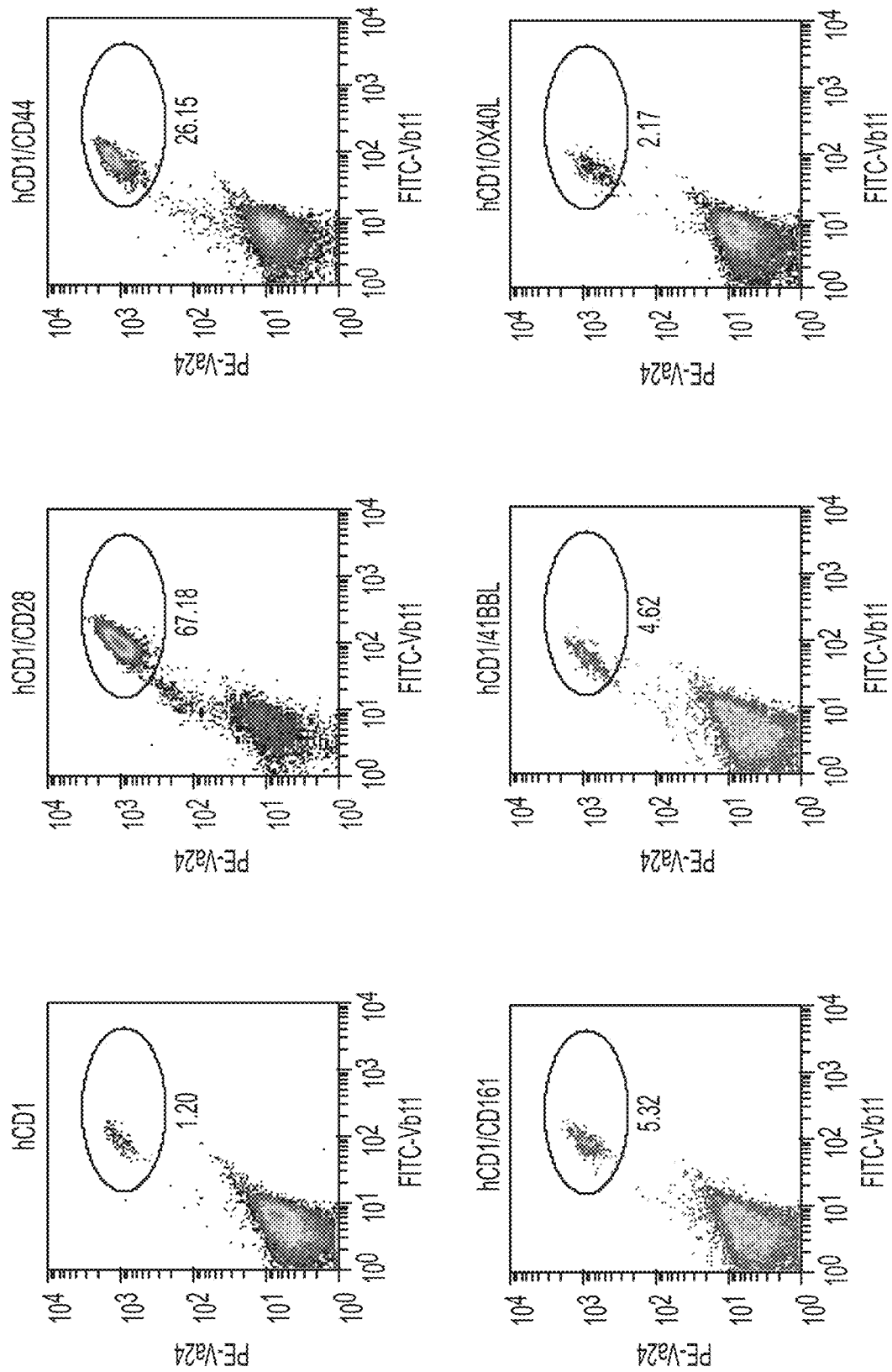
FIG. 17 shows different co-stimulatory molecules affect NKT cell proliferation by aAPC. NKT cells were expanded using two cycles of aAPC and the percentage of NKT cells was assessed by flow cytometry using an LSR II and data was analyzed using FCS Express software.
Figure 18:
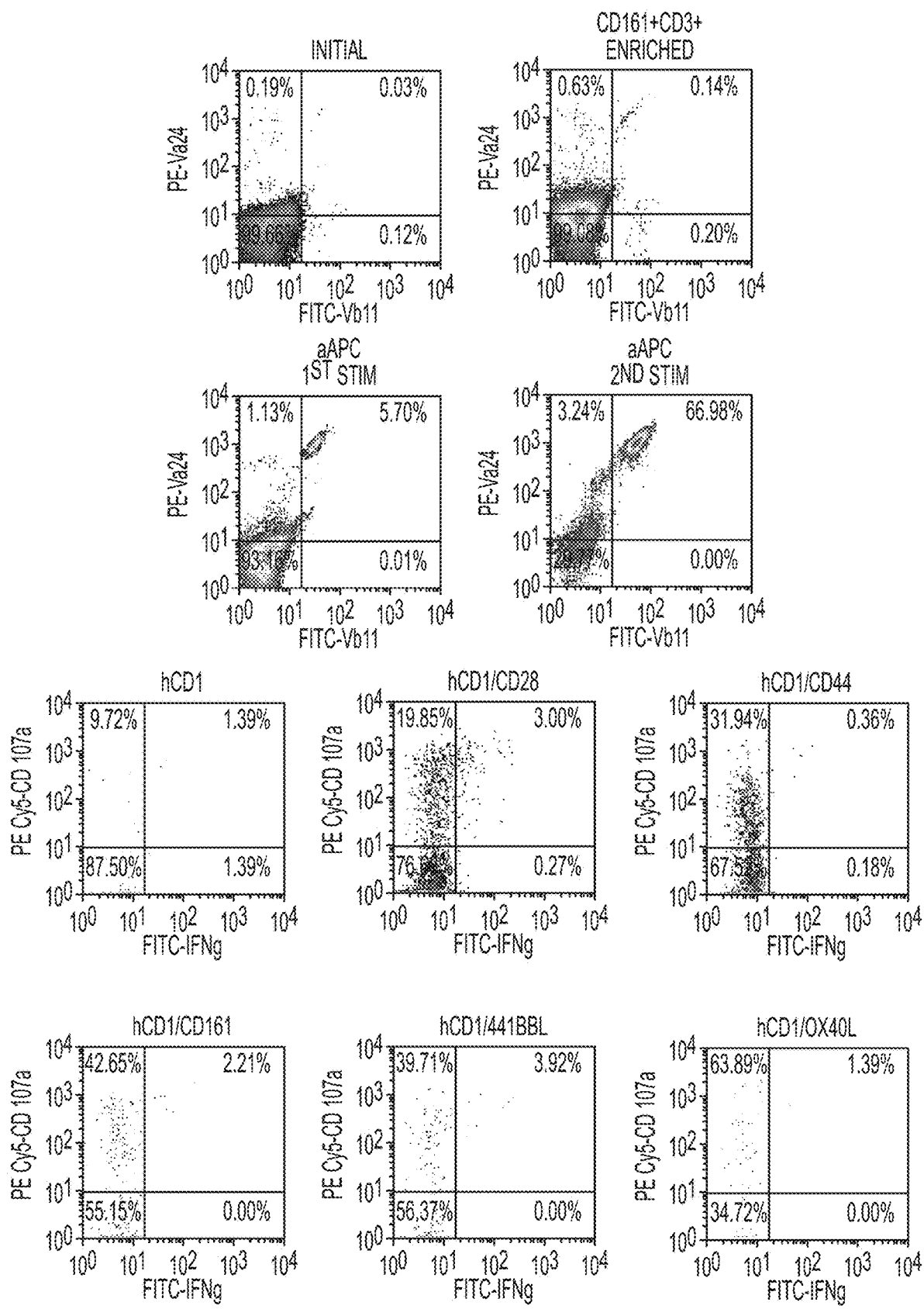
FIG. 18 shows, on the top row an efficient methods for expanding NKT cells ex vivo from human peripheral blood was developed. It was found that enriching for NKT-like cells (CD161+CD3+) then incubating with CD1d-Ig/CD28 aAPC for two cycles (each cycle is 12-14 days) results in the highest NKT cell expansion. Bottom: Enriched NKT like cells were cultured using different formulations of aAPC. After two rounds the cultures were stimulated with PMA & ionomycin and function was assessed by flow cytometry. The NKT cells were gated (Va24+Vb11+) and CD107a was measured as an indication of cytotoxicity and IFN-g was measured to assess cytokine production by the expanded NKT cells. In the absence of co-stimulation, NKT cell proliferation and effector functions are impaired (hCD1).
Figure 19:
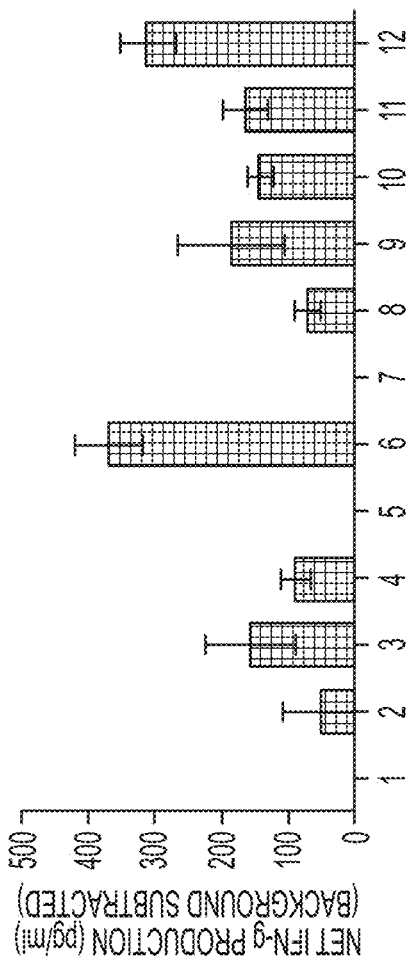
FIG. 19 shows aAPC can be used to assess the roles of co-stimulatory molecules on NKT cell function. Human peripheral blood NKT cells were co-cultured with different formulations of aAPC for 48 hours. aAPC-induced NKT cell activation was assessed by measuring cytokine production (IFN-$\gamma$) by ELISA.

FIG. 15 shows B6 mice were injected with B16-F10 melanoma cells i.v., on day 7 Qdots were injected i.v. and tumor clearance was assessed. FIG. 16 shows the use of different co-stimulatory molecules (CD28, 44, 41BB, OX40L) on aAPC differentially effect NKT cell expansion. The fold expansion is calculated by determining the percentage of NKT cells by flow cytometry and multiplying % NKT cells by the total number of cells in the culture. FIG. 17 shows different co-stimulatory molecules affect NKT cell proliferation by aAPC. NKT cells were expanded using two cycles of aAPC and the percentage of NKT cells was assessed by flow cytometry using an LSR II and data was analyzed using FCS Express software. FIG. 18 shows, on the top row an efficient methods for expanding NKT cells ex vivo from human peripheral blood was developed. It was found that enriching for NKT-like cells (CD161+CD3+) then incubating with CD1d-Ig/CD28 aAPC for two cycles (each cycle is 12-14 days) results in the highest NKT cell expansion. Bottom: Enriched NKT like cells were cultured using different formulations of aAPC. After two rounds the cultures were stimulated with PMA & ionomycin and function was assessed by flow cytometry. The NKT cells were gated (Va24+Vb11+) and CD107a was measured as an indication of cytotoxicity and IFN-g was measured to assess cytokine production by the expanded NKT cells. In the absence of co-stimulation, NKT cell proliferation and effector functions are impaired (hCD1). FIG. 19 shows aAPC can be used to assess the roles of co-stimulatory molecules on NKT cell function. Human peripheral blood NKT cells were co-cultured with different formulations of aAPC for 48 hours. aAPC-induced NKT cell activation was assessed by measuring cytokine production (IFN-γ) by ELISA. FIG. 19. aAPC can be used to assess the roles of co-stimulatory molecules on NKT cell function. Human peripheral blood NKT cells were co-cultured with different formulations of aAPC for 48 hours. aAPC-induced NKT cell activation was assessed by measuring cytokine production (IFN-γ) by ELISA.

Natural Killer T Cells Generated from Human Adult Hematopoietic Stem-Progenitor Cells are Poly-Functional Cancer patients have a reduction in both NKT cell number and function, and these deficits limit the potential clinical application of NKT cells for cancer therapy. To overcome the problem of limited NKT cell numbers, it is shown here that NKT cells can be generated in vitro from bone marrow-derived adult hematopoietic stem-progenitor cells (HSPC). Co-culture of HSPC with OP9-DL1 stromal cells, results in a functional CD3$^+$ T cell population. These T cells can be further differentiated into NKT cells by secondary culture with CD1d-Ig-based artificial antigen-presenting cells (aAPC). Importantly, these in vitro-generated NKT cells are functional, as demonstrated by their ability to proliferate and secrete IFN-γ and GM-CSF following stimulation.

Figure 20:
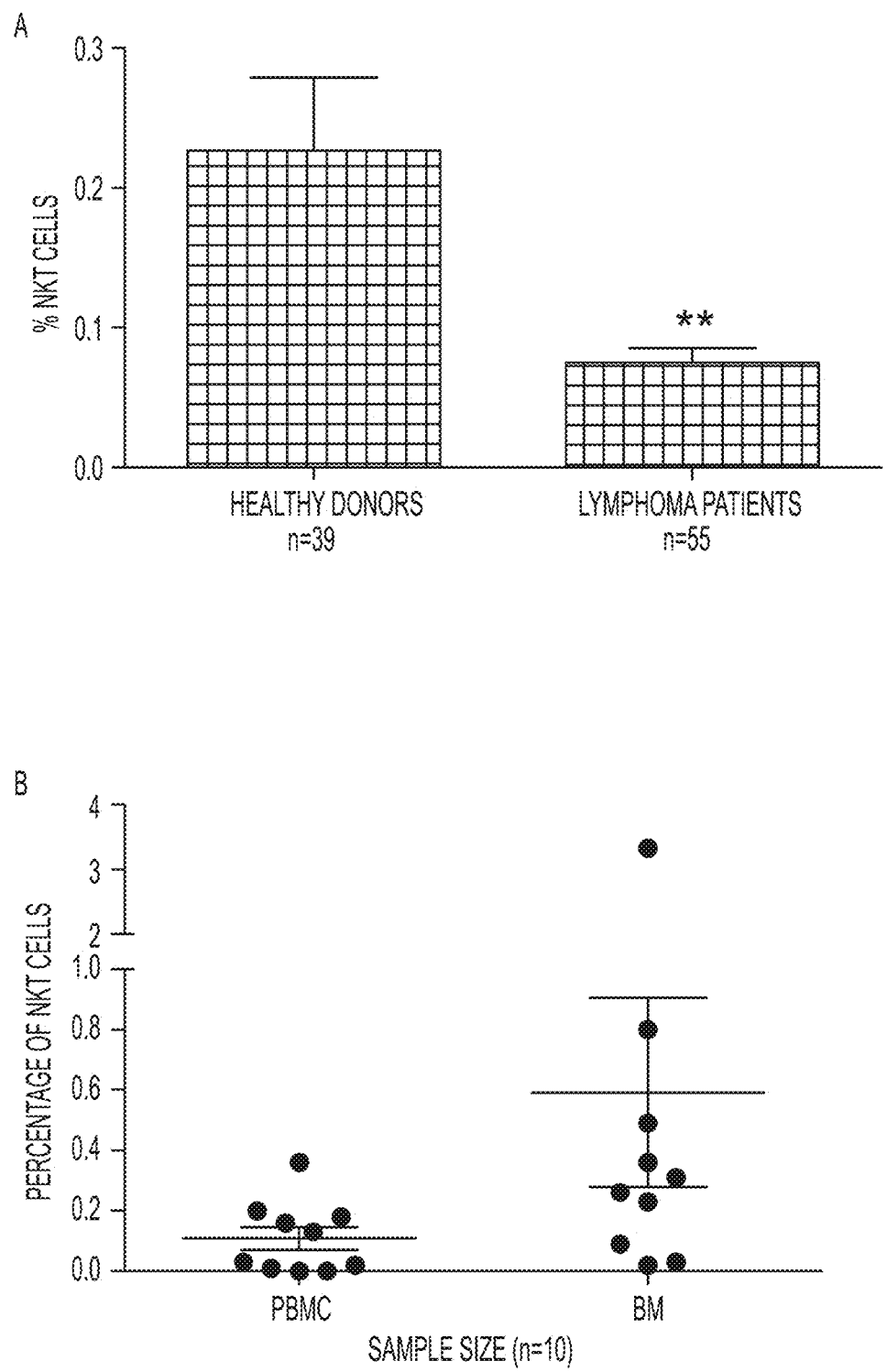
FIG. 20 shows NKT cells are decreased in cancer patients. Panel A shows PBMC were isolated from healthy donors and cancer patients and analyzed for V$\alpha$24$^+$V$\beta$11$^+$ cells by flow cytometry. The data are representative of 39 healthy donors and 55 newly-diagnosed cancer patients. The percentages from all of the healthy donors and cancer patients in this study were averaged. **p=0.0012. Panel B shows NKT cells are higher in the bone marrow compared to the peripheral blood. MNC were isolated from the bone marrow and peripheral of lymphoma patients and stained for flow cytometry. Data were collected from ten NHL patients, and the data are shown as mean±SEM. Data were acquired using an LSR II and analyses were performed using FCS Express software.

NKT cells are reduced in Cancer Patients: a comparison of the percentage of NKT cells in healthy donors and newly diagnosed lymphoma patients prior to treatment or surgery. As shown in FIG. 20, panel A, the percentage of NKT cells was 0.08±0.01 in lymphoma patients (N=55) compared to 0.23±0.05 in healthy donors (N=39). Analysis of the frequency of classical T cell subsets in the total PBMCs showed a high degree of variability, but no consistent differences were noted. NKT cells in the bone marrow and peripheral blood of lymphoma patients were next evaluated. As shown in FIG. 20, panel B, in each of ten non-Hodgkin lymphoma (NHL) patients, the percentage of NKT cells was lower in the peripheral blood (0.10±0.04) than in the bone marrow (0.59±0.31). These data substantiate the idea that circulating NKT cells are reduced in patients with systemic malignancies. Furthermore, while the levels of NKT cells are higher in the bone marrow than in the peripheral blood, their absolute numbers remain inadequate for clinical application (less than $10^4$ NKT cells/million lymphocytes).

Figure 21:
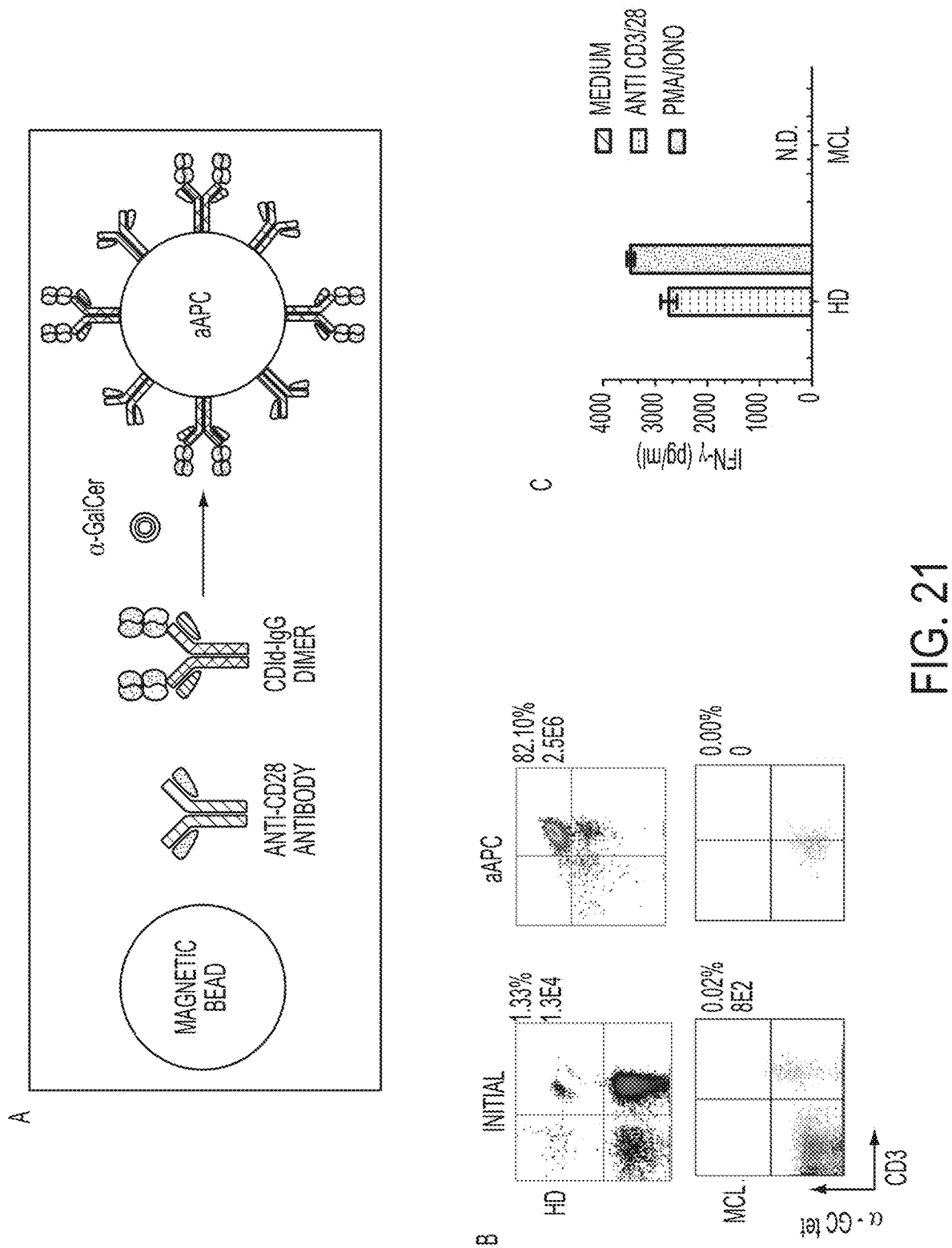
FIG. 21 shows NKT cells from MCL patients are non-functional. Panel A shows Schematic diagram of CD1d:Ig-based aAPC. In this system, CD1d-Ig is used to provide the cognate antigen-specific signal through the TCR and anti-CD28 Abs provide the costimulatory signal. Panel B shows CD3$^+$ cells were isolated from the blood of healthy donors and MCL patients. NKT cell % ($\alpha$GC-tet$^+$CD3$^+$) were determined by FACS and the cells were stimulated biweekly with aAPC. Data shown are after 2 rounds of stimulation. The top number indicates the NKT cell % and the bottom number indicates the total number of NKT cells. Panel C shows CD1d-aAPC expanded NKT cells were stimulated with anti-CD3/CD28 microbeads or PMA and ionomycin. T cell activation was assessed by IFN-$\gamma$ production. N.D.—not detected. Data are representative of three independent experiments.
Figure 22:
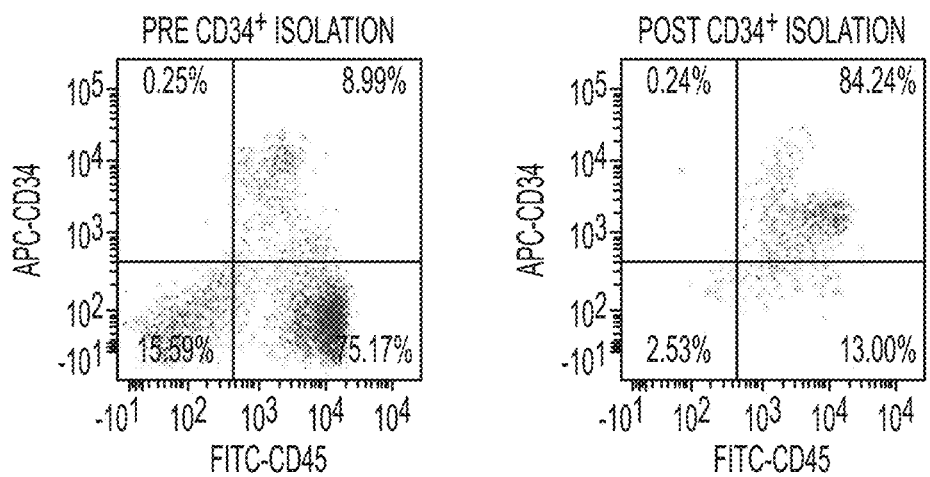
FIG. 22 shows generation of natural killer T cells from adult human HSPC. Panel A shows Human CD34$^+$ cells were isolated from bone marrow. Cells were stained for CD34 and CD45. Panel B shows Schematic of the generation of HSPC derived human NKT cells. Human CD34$^+$ HSC isolated from bone marrow were co-cultured with OP9-DL1 or OP9-GFP cells. The time course of the cell culture, phenotypic and functional analysis is shown.
Figure 22:
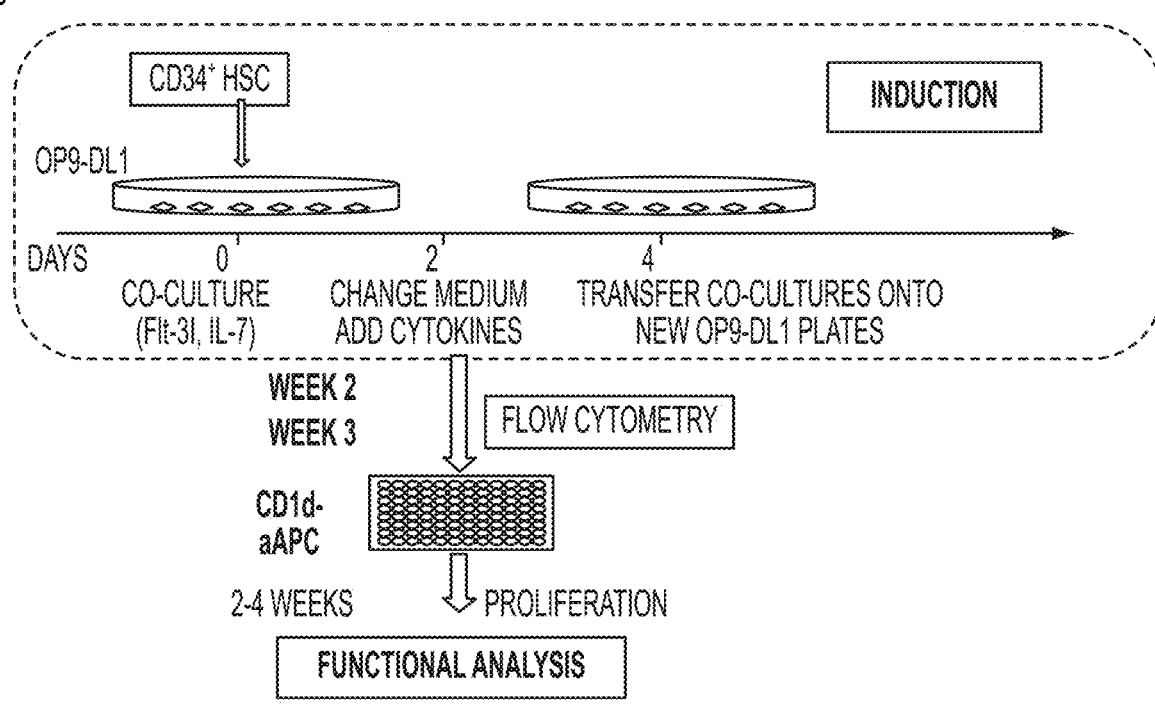

Ex vivo NKT cell expansion is impaired in MCL patients: without wishing to be bound by theory, a potential mechanism for reduced number of NKT cells in MCL patients is the direct effect of circulating malignant MCL cells, which could interfere with NKT cell activity. In order to examine the function of NKT cells in absence of malignant cells, it was an expansion of NKT cells from MCL patients ex vivo was attempted. CD1d-Ig based artificial antigen presenting cells (aAPC) were generated by coupling CD1d-Ig onto magnetic beads in combination with anti-CD28 mAb[24] (schematic, FIG. 21, panel A). Enriched T cells were stimulated with α-GalCer-loaded aAPC biweekly for one month. Starting with equivalent T cell numbers in each group, NKT cells isolated from the peripheral blood of MCL patients did not expand, in contrast to NKT cells isolated from healthy donors and patients with melanoma (FIG. 22, panel B and Table 3). To ascertain whether the loss in NKT cell proliferation and function was specific to MCL, enriched T cells from patients with diffuse large B cell lymphoma (DLBCL) were stimulated with α-GalCer-loaded aAPC (Table 3). Similar to T cells derived from MCL patients, there was minimal NKT expansion from patients with DLBCL. As shown in FIG. 22, panel C, not only was NKT cell proliferation impaired, the total cultured T cell population was also non-functional and could not be activated by stimulation with anti-CD3/CD28 or PMA/ionomycin. These data suggest that MCL, and possibly other types of lymphomas, produce a factor that results in an irreversible defect in the NKT cell population and a suppression of the overall T-cell population.

TABLE 3

Ex vivo expansion of NKT cells

|  |  | Initial % NKT cells | % Post aAPC expansion | Fold Expansion |
|---|---|---|---|---|
| Healthy Controls | HD1* | 1.34 | 82.10 | 61 |
|  | HD2 | 0.14 | 95.56 | 682 |
|  | HD3 | 0.12 | 38.21 | 318 |
|  | HD4 | 0.03 | 67.37 | 2245 |
| Cancer patients | DLBCL47** | 0.2 | 5.21 | 26 |
|  | DLBCL49 | 0.04 | 6.91 | 172 |
|  | Melanoma | 0.26 | 61 | 234 |
|  | MCL1*** | 0.03 | 0.03 | 1 |
|  | MCL2 | 0.02 | 0.0 | 0 |
|  | MCL46 | 0.02 | 0.0 | 0 |
|  | MCL48 | 0.13 | 0.0 | 0 |

*HD—Healthy Donor
**DLBCL—Diffuse Large B cell Lymphoma
***MCL—Mantle Cell Lymphoma Generation of mature human T cells using OP9-DL1 cultures: based on the low absolute numbers of circulating NKT cells and an inability to expand from the peripheral blood, we sought to develop a bridge to the clinical use of these cells by differentiating NKT cells from adult progenitor stem cells. Human CD34$^+$ HPC were enriched using magnetic cell sorting and seeded on the OP9-DL1 feeder layer (FIG. 22, panel A). Cellular proliferation and differentiation were studied using CD34, CD38, Vα24, Vα11, CD4, CD8, CD3, and TCR γδ as post-selection markers (see schematic in FIG. 22, panel B). Phenotypically mature T cells could be easily discerned in the cultures because, as time progressed, the cells lost expression of CD34 and CD38, transitioned to double-positive thymocytes, and then primarily to CD4$^+$CD3$^+$ T cells. CD34 expression decreased as the cells became CD3$^+$ in the presence of Notch signaling (expression of DL1) in the OP9 stromal cells. Notably, when the HSPC were cultured with the OP9-DL9, there was much greater differentiation than with the control—OP9-GFP (data not shown).

Figure 23:
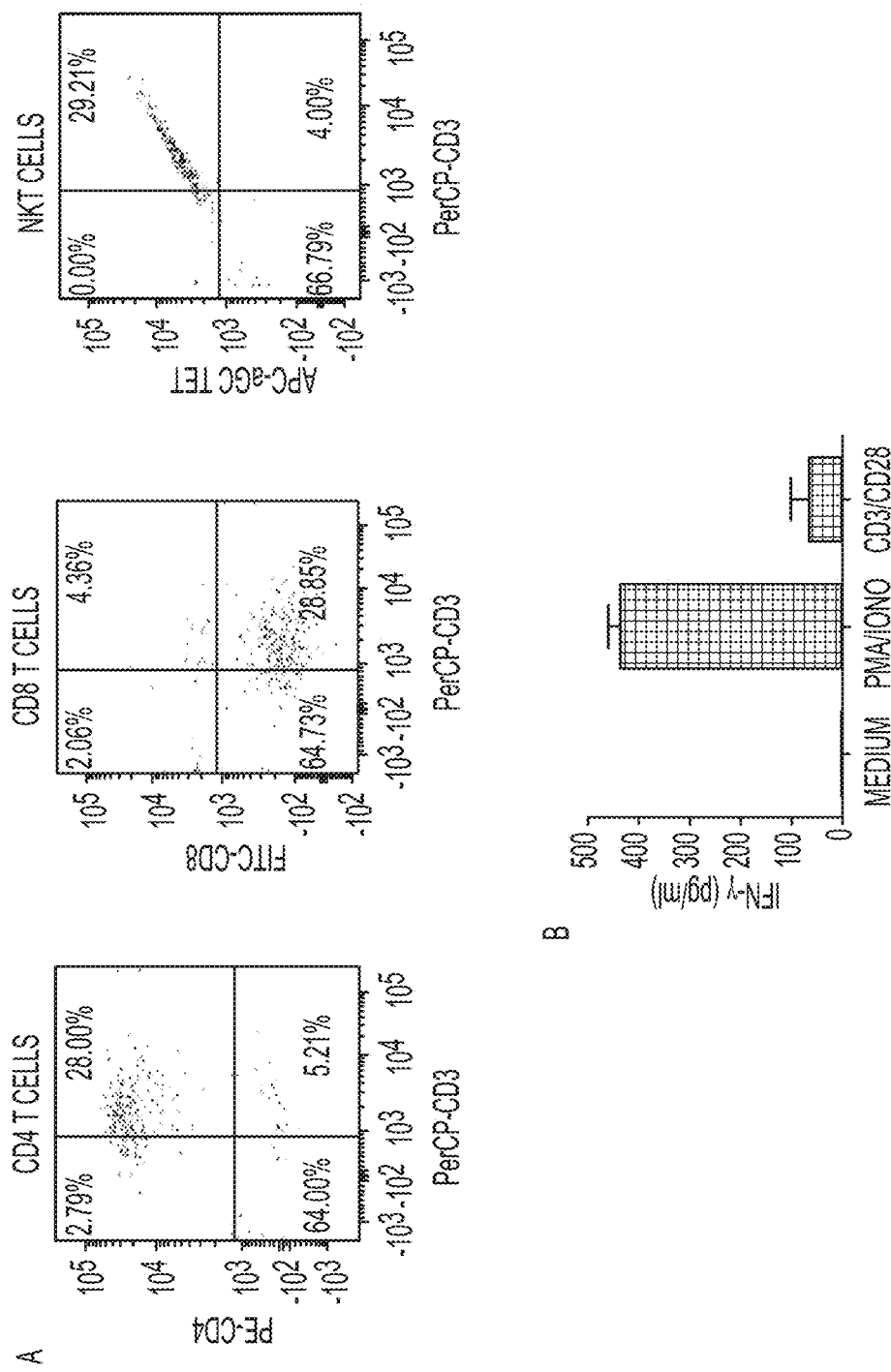
FIG. 23 shows expansion of NKT cells from HSPC using aAPC. Panel A shows NKT cell expansion following aAPC stimulation. T cells were generated from HSPC using the OP9-DL1 co-culture system. The T cells were then expanded using CD1d-based aAPC. The expanded population was stained for NKT cells ($\alpha$-GalCer-tet$^+$CD3$^+$), and the remaining cells were stimulated biweekly with aAPC. Data shown are after a single round of stimulation. Panel B shows Cultured NKT cells are functional. HSPC-generated T cells co-cultured with CD1d-aAPC were stimulated with anti-CD3/CD28 microbeads or PMA and ionomycin for 48 hr. Culture supernatants were harvested and NKT cell activation was assessed by IFN-$\gamma$ production, which was measured by standard sandwich ELISA. Data from healthy donor is shown and is representative data obtained from five different donors.

Expansion of Primary NKT cells using artificial antigen presenting cells (aAPC) it was found that initially the expanded T cells were largely Vα24$^-$; but we have been able to use bead based-CD1d-expressing artificial antigen presenting cells (aAPC) to expand human NKT cells in vitro. Thus, OP9-DL1-generated primary T cells were co-cultured with α-GalCer-loaded aAPC (FIG. 23, panel A). The expanded population was mostly CD8$^-$NKT cells. We found that these cells produced IFN-γ FIG. 23, panel B), GM-CSF and IL-4 (data not shown) following stimulation. Given the above phenotypic and functional characteristics, we posit that adult human bone marrow stem cells can be used to generate functionally mature NKT cells.

Figure 24:
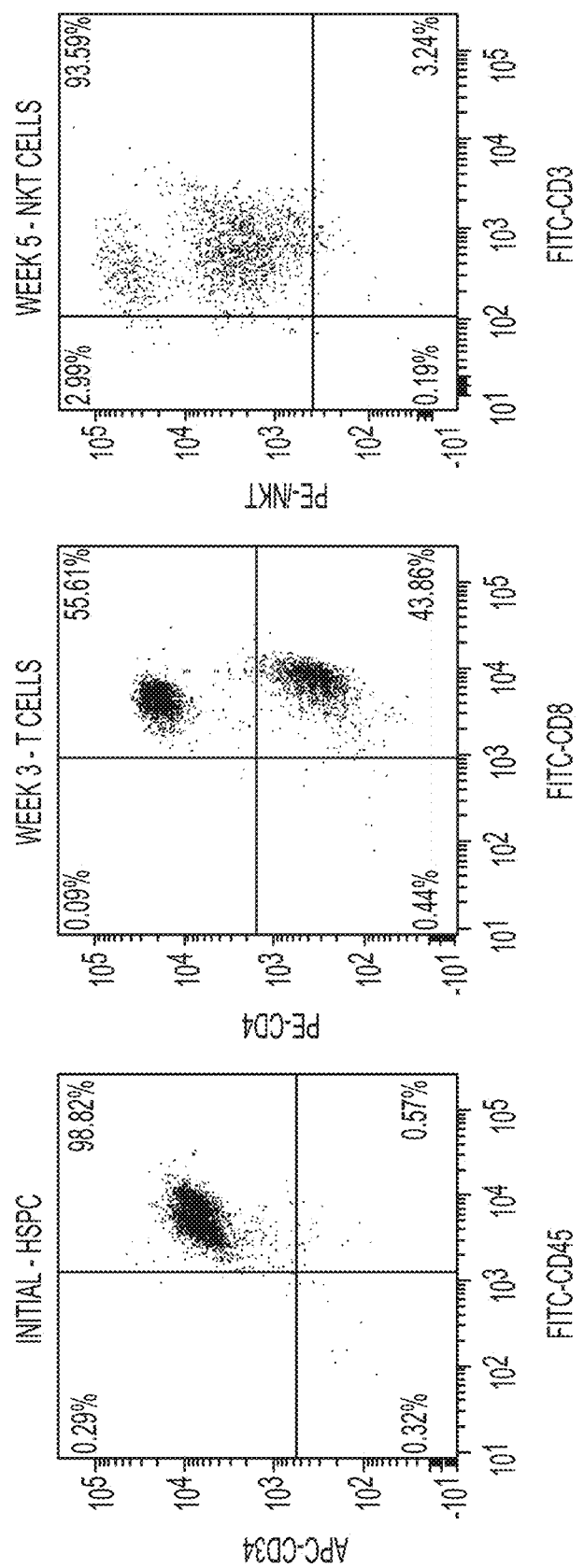
FIG. 24 shows enrichment of NKT cells increases antigen-specific proliferation. NKT cells were generated from HSPC using the OP9-DL1/aAPC co-culture system, then enriched using magnetic bead separation in combination with mAb specific for the iNKT TCR (clone 6B11). The sorted cells were stimulated biweekly with $\alpha$-GalCer loaded-aAPC. The initial population and the expanded population were stained for canonical NKT cells (CD3 and iNKT). Data shown are after 2 weeks of stimulation post enrichment.

Cellular expansion was also measured. Based on cell counts and flow cytometry data, our data suggest that the cells first differentiated into T cells and then the T cell population expanded. An increase the number and percentage of NKT cells was attempted. In these studies, T cells were generated from CD34$^+$ cells isolated from the bone marrow from newly diagnosed lymphoma patients. After incubating the HSPC derived T cell population with aAPC for one week, the cells were stained with an NKT cell specific mAb, clone 6811. Anti-mouse IgG1 microbeads were used to separate the NKT cells. Although the initial NKT cell population (Vα24$^+$Vα11$^+$) was still relatively low (>1%), after two weeks of stimulation with aAPC the percentage was approximately 60-90% of 2-3 million cells, that represents a 9400 fold expansion based on percentages and over a 18,800 fold expansion based on NKT cell numbers (FIG. 24). Thus, the initial manipulation to enrich the NKT population was helpful in generating an enhanced post-stimulation specific population.

Figure 25:
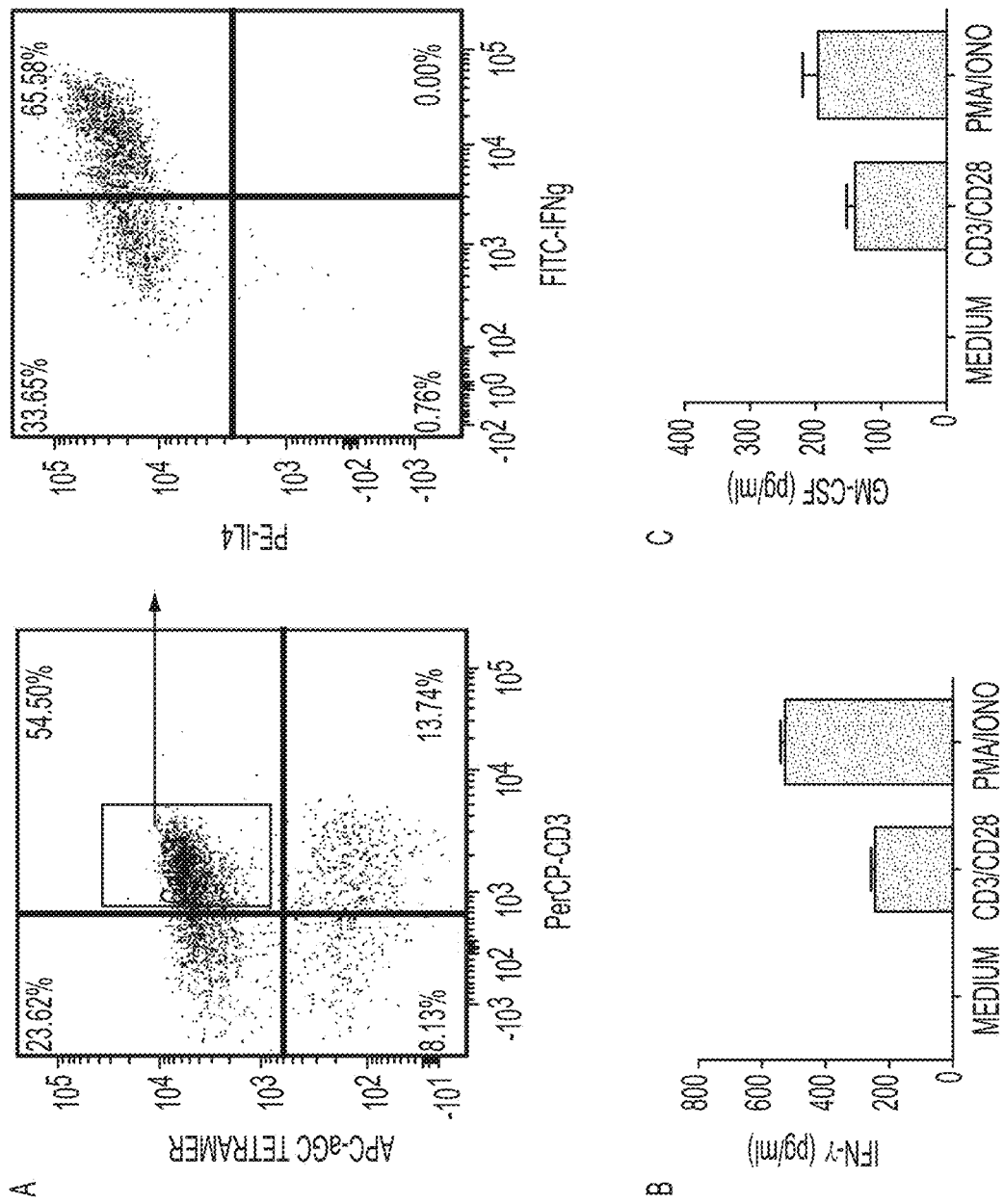
FIG. 25 shows human HSPC derived NKT cells are polyfunctional. Human bone marrow CD34$^+$ cells were isolated from a patient with non-Hodgkin's Lymphoma. NKT cells were generated using the OP9-DL1 system in combination with aAPC. The NKT cells were stained with either unloaded tetramer or $\alpha$-GalCer loaded tetramer. The CD1d-tetramer$^+$CD3$^+$ population was gated following stimulation with PMA and ionomycin and induction of IL-4 and IFN- by NKT cells was assessed by flow cytometry. Panel B shows Primary human NKT cells ($10^4$) were co-cultured with anti-CD28/CD3 microbeads ($10^5$) or PMA and ionomycin for 48 hours. Medium served as a negative control. Culture supernatants were harvested and standard sandwich ELISA was used to measure cytokine production. One experiment representative of data obtained from two lymphoma patients is shown.

In order to confirm that the HSPC-aAPC derived NKT cells from lymphoma patients were mature and fully functional, we next sought to determine whether there were distinct populations producing specific cytokines or if the same population of cells produced both IFN-γ and IL-4. HSPC derived NKT cells were cultured were stimulated with PMA and ionomycin and cytokine production was assessed (FIG. 25). Assessment of cytokine production by intracellular cytokine staining revealed that these tetramer positive NKT cells were capable of producing both Th1 and Th2 cytokines. In addition, it was found that these patient derived cells were also capable of producing IFN-γ and GM-SCF. Therefore, these data indicate that HSPC-derived NKT cells are polyfunctional and can produce multiple types of cytokines.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

What is claimed is:

1. A microparticle or nanoparticle artificial antigen presenting cell for stimulation and expansion of NKT cells, comprising:
    (a) a paramagnetic iron dextran bead; and, on the surface of the bead,
    (b) a population of CD1d antigen presenting complexes that activate T cell receptors (TCRs) of natural killer T (NKT) cells, wherein the CD1d antigen presenting complexes present an NKT cell antigen selected from the group consisting of α-C-GalCer, GSL-1, and iGB3;
    (c) a population of NKT cell costimulatory ligands which specifically bind to CD44;
    (d) a population of NKT cell costimulatory ligands which specifically bind to CD161;
    (e) a population of binding NKT cell costimulatory ligands which specifically bind to CD28 and a population of NKT cell costimulatory ligands which specifically bind to CD40,
    wherein the NKT cell costimulatory ligands are antibodies or antigen-binding fragments thereof,
    wherein the CD1d antigen is a fusion protein with an immunoglobulin sequence,
    wherein the ratio of CD1d-Ig to anti-CD28 is 10:1,
    wherein the microparticle or nanoparticle artificial antigen presenting cell has a size of 150 nm or 200 nm.

2. A microparticle or nanoparticle artificial antigen presenting cell for stimualation and expansion of NKT cells, consisting essentially of:
    (a) a paramagnetic iron dextran bead; and, on the surface of the bead,
    (b) a population of CD1d antigen presenting complexes that activate T cell receptors (TCRs) of natural killer T (NKT) cells, wherein the CD1d antigen presenting complexes present an NKT cell antigen selected from the group consisting of a-C-GalCer, GSL-1, and iGB3;
    (c) a population of NKT cell costimulatory ligands which specifically bind to CD44;
    (d) a population of NKT cell costimulatory ligands which specifically bind to CD161;
    (e) a population of binding NKT cell costimulatory ligands which specifically bind to CD28 and a population of NKT cell costimulatory ligands which specifically bind to CD40,
    wherein the NKT cell costimulatory ligands are antibodies or antigen-binding fragments thereof,
    wherein the CD1d antigen is a fusion protein with an immunoglobulin sequence,
    wherein the ratio of CD1d-Ig to NKT cell costimulatory CD28-binding ligand is 10:1,
    wherein the microparticle or nanoparticle artificial antigen presenting cell has a size of 150 nm or 200 nm.

3. The microparticle or nanoparticle artificial antigen presenting cell of claim 1, wherein the CD1d antigen presenting complexes are fused with an immunoglobulin heavy chain sequence, or fragment thereof, thereby providing a dimeric CD1d ligand.

4. The microparticle or nanoparticle artificial antigen presenting cell of claim 2, wherein the CD1d antigen presenting complexes are fused with an immunoglobulin heavy chain sequence, or fragment thereof, thereby providing a dimeric CD1d ligand.

5. The microparticle or nanoparticle artificial antigen presenting cell of claim 1, wherein the NKT cells are Type I and/or Type II NKT cells.

6. The microparticle or nanoparticle artificial antigen presenting cell of claim 2, wherein the NKT cells are Type I and/or Type II NKT cells.

7. The microparticle or nanoparticle artificial antigen presenting cell of claim 1, wherein the NKT cells are CD4+, CD8+, or CD4+CD8+, CD4−CD8−.

8. The microparticle or nanoparticle artificial antigen presenting cell of claim 2, wherein the NKT cells are CD4+, CD8+, or CD4+CD8+, CD4−CD8−.

9. A pharmaceutical composition comprising a pharmaceutically acceptable carrier and the microparticle or nanoparticle artificial antigen presenting cell of claim 1.

10. A pharmaceutical composition comprising a pharmaceutically acceptable carrier and the microparticle or nanoparticle artificial antigen presenting cell of claim 2.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthetic: modified Mart-1 peptide

<400> SEQUENCE: 1

Glu Leu Ala Gly Ile Gly Ile Leu Thr Val
1               5                   10
```